(12) United States Patent
Pedro et al.

(10) Patent No.: US 10,589,047 B2
(45) Date of Patent: Mar. 17, 2020

(54) COMBINED NASAL AND MOUTH VENTILATION MASK

(71) Applicant: Revolutionary Medical Devices, INC., Tucson, AZ (US)

(72) Inventors: Michael J. Pedro, Brooklyn, NY (US); Steven H. Cataldo, New York, NY (US); David M. Kane, Tucson, AZ (US); Thomas Reilly, Tucson, AZ (US); Ryan Redford, Tucson, AZ (US)

(73) Assignee: Revolutionary Medical Devices, Inc., Tucson, AZ (US)

( * ) Notice: Subject to any disclaimer, the term of this patent is extended or adjusted under 35 U.S.C. 154(b) by 0 days.

(21) Appl. No.: 15/272,190

(22) Filed: Sep. 21, 2016

(65) Prior Publication Data
US 2017/0035979 A1    Feb. 9, 2017

Related U.S. Application Data

(63) Continuation of application No. 15/127,760, filed as application No. PCT/US2015/034277 on Jun. 4, 2015.
(Continued)

(51) Int. Cl.
*A61M 16/06* (2006.01)
*A61M 16/10* (2006.01)
(Continued)

(52) U.S. Cl.
CPC ....... *A61M 16/0616* (2014.02); *A61G 13/121* (2013.01); *A61M 16/009* (2013.01);
(Continued)

(58) Field of Classification Search
CPC ........ A61M 16/00; A61M 16/06–0694; A61M 16/20–209; A61M 2016/0003–0042;
(Continued)

(56) References Cited

U.S. PATENT DOCUMENTS

| 1,050,621 A | 1/1913 | Ford ........................ 128/206.28 |
| 1,131,802 A | 3/1915 | Stenshoel |

(Continued)

FOREIGN PATENT DOCUMENTS

| CN | 202478364 | 10/2012 | ............ A61M 16/06 |
| CN | 202505937 | 10/2012 | ............ A61M 16/06 |

(Continued)

OTHER PUBLICATIONS

International Search Report and Written Opinion issued in application No. PCT/US2016/037070, dated Nov. 10, 2016 (11 pgs).
(Continued)

*Primary Examiner* — Samchuan C Yao
*Assistant Examiner* — Ned T Heffner
(74) *Attorney, Agent, or Firm* — Morgan, Lewis & Bockius LLP

(57) ABSTRACT

A gas ventilation mask includes an anesthesia nasal mask and a mouth mask defining respectively a nasal chamber and an oral chamber, detachably connected to one another so that the nasal mask and the mouth mask may be used either separately as a nasal mask or as a mouth mask, or as a combination nasal-mouth mask. Also provided is an anesthesia mask strap system having a first expandable strap portion having the ability to extend; second and third non-expandable strap sections fixed to ends of the first expandable strap section; and an adhesion section for fixing a length of the strap system when the second and third non-expandable strap sections are pulled to tension the expandable strap section.

13 Claims, 30 Drawing Sheets

Related U.S. Application Data

(60) Provisional application No. 62/007,802, filed on Jun. 4, 2014, provisional application No. 62/056,293, filed on Sep. 26, 2014, provisional application No. 62/060,417, filed on Oct. 6, 2014, provisional application No. 62/061,045, filed on Oct. 7, 2014, provisional application No. 62/065,504, filed on Oct. 17, 2014, provisional application No. 62/091,370, filed on Dec. 12, 2014, provisional application No. 62/118,301, filed on Feb. 19, 2015, provisional application No. 62/149,313, filed on Apr. 17, 2015, provisional application No. 62/161,086, filed on May 13, 2015, provisional application No. 62/161,093, filed on May 13, 2015.

(51) Int. Cl.
*A61M 16/20* (2006.01)
*A61M 16/00* (2006.01)
*A61M 16/01* (2006.01)
*A61G 13/12* (2006.01)
*A61M 16/18* (2006.01)
*A62B 18/00* (2006.01)
*A61M 16/08* (2006.01)

(52) U.S. Cl.
CPC ............ *A61M 16/01* (2013.01); *A61M 16/06* (2013.01); *A61M 16/0683* (2013.01); *A61M 16/104* (2013.01); *A61M 16/18* (2013.01); *A61M 16/208* (2013.01); *A62B 18/00* (2013.01); *A61M 16/085* (2014.02); *A61M 2202/0208* (2013.01); *A61M 2210/0618* (2013.01); *A61M 2210/0625* (2013.01); *A61M 2230/432* (2013.01)

(58) Field of Classification Search
CPC .... A62B 7/00; A62B 7/04; A62B 7/14; A62B 18/00; A62B 18/10; B63C 11/12; B63C 11/18
See application file for complete search history.

(56) References Cited

U.S. PATENT DOCUMENTS

| | | | |
|---|---|---|---|
| 1,441,817 A | 1/1923 | McCullough | |
| 1,729,525 A | 9/1929 | Stenshoel | |
| 1,776,167 A | 9/1930 | Stenshoel | |
| 2,452,816 A | 11/1948 | Wagner | 311/10 |
| 2,843,121 A | 7/1958 | Hudson | 128/146 |
| 2,939,458 A | 6/1960 | Lundquist | 128/206.24 |
| 3,013,556 A | 12/1961 | Galleher | |
| 3,522,612 A | 8/1970 | Palmer | 2/88 |
| 3,556,097 A | 1/1971 | Wallace | 128/188 |
| 3,779,164 A | 12/1973 | Study | 128/206 |
| 3,815,596 A | 6/1974 | Keener et al. | 128/188 |
| 3,856,051 A | 12/1974 | Bain | 138/114 |
| 3,889,668 A | 6/1975 | Ochs et al. | 128/134 |
| 3,897,777 A | 8/1975 | Morrison | 128/133 |
| D242,490 S | 11/1976 | Belkin | D83/1 R |
| 4,005,499 A | 2/1977 | Klein | 5/485 |
| 4,007,737 A | 2/1977 | Paluch | 128/188 |
| 4,015,598 A | 4/1977 | Brown | 128/188 |
| 4,188,946 A | 2/1980 | Watson et al. | 128/204.22 |
| D256,161 S | 7/1980 | Oliver | D6/602 |
| 4,231,363 A | 11/1980 | Grimes | 128/205.25 |
| 4,232,667 A | 11/1980 | Chalon et al. | 128/203.26 |
| 4,248,218 A | 2/1981 | Fischer | 128/204.18 |
| 4,259,757 A | 4/1981 | Watson | 5/434 |
| 4,265,235 A | 5/1981 | Fukunaga | 128/200.24 |
| 4,265,239 A | 5/1981 | Fischer, Jr. et al. | 128/205.17 |
| 4,275,720 A | 6/1981 | Wichman | 128/853 |
| 4,328,797 A | 5/1982 | Rollins | 128/202.15 |
| 4,457,026 A | 7/1984 | Morris | 2/171 |
| 4,463,755 A | 8/1984 | Suzuki | 128/204.18 |
| 4,471,769 A | 9/1984 | Lockhart | 128/849 |
| 4,574,796 A | 3/1986 | Lundstrom | 128/855 |
| 4,596,246 A | 6/1986 | Lyall | 128/202.27 |
| 4,657,010 A | 4/1987 | Wright | 128/205.25 |
| 4,700,691 A | 10/1987 | Tari et al. | 128/1 R |
| 4,770,169 A | 9/1988 | Schmoegner et al. | 128/207.13 |
| 4,905,712 A | 3/1990 | Bowlin et al. | 128/870 |
| 5,046,200 A | 9/1991 | Feder | 2/452 |
| 5,046,491 A | 9/1991 | Derrick | 128/200.24 |
| 5,121,746 A | 6/1992 | Sikora | 128/203.12 |
| D333,404 S | 2/1993 | Thompson | D6/602 |
| 5,243,971 A | 9/1993 | Sullivan et al. | 128/205.25 |
| 5,255,303 A | 10/1993 | DiMaio et al. | 378/177 |
| 5,271,390 A | 12/1993 | Gray et al. | 128/207.12 |
| 5,284,160 A | 2/1994 | Dryden | 128/203.12 |
| D347,494 S | 5/1994 | Mustelier | D24/110.4 |
| D354,128 S | 1/1995 | Rinehart | D24/110.1 |
| 5,404,873 A | 4/1995 | Leagre et al. | 128/204.18 |
| 5,462,050 A | 10/1995 | Dahlstrand | 128/207.18 |
| 5,474,060 A | 12/1995 | Evans | 128/204.22 |
| 5,485,837 A | 1/1996 | Solesbee et al. | 128/207.17 |
| 5,524,639 A | 6/1996 | Lanier et al. | 128/845 |
| D373,921 S | 9/1996 | Palomo et al. | D6/602 |
| 5,557,049 A * | 9/1996 | Ratner | A61M 16/208 128/204.23 |
| RE35,339 E | 10/1996 | Rapoport | 128/204.18 |
| 5,560,354 A * | 10/1996 | Berthon-Jones | A61M 16/06 128/204.18 |
| 5,586,551 A | 12/1996 | Hilliard | 128/200.14 |
| 5,647,357 A | 7/1997 | Barnett et al. | 128/206.24 |
| 5,649,331 A | 7/1997 | Wilkinson et al. | 5/710 |
| 5,660,174 A | 8/1997 | Jacobelli | 128/206.24 |
| 5,661,859 A | 9/1997 | Schaefer | 5/621 |
| 5,685,298 A | 11/1997 | Idris | 128/206.12 |
| 5,738,094 A | 4/1998 | Hoftman | 128/206.26 |
| 5,746,201 A | 5/1998 | Kidd | 128/206.24 |
| 5,749,358 A | 5/1998 | Good et al. | 128/205.23 |
| 5,778,872 A | 7/1998 | Fukunaga et al. | 128/202.27 |
| D402,755 S | 12/1998 | Kwok | D24/110 |
| 5,884,624 A | 3/1999 | Barnett et al. | 128/206.24 |
| 5,933,886 A | 8/1999 | Washington | 5/494 |
| 5,966,763 A | 10/1999 | Thomas et al. | 5/715 |
| 5,975,079 A | 11/1999 | Hellings et al. | 128/206.24 |
| 5,983,896 A | 11/1999 | Fukunaga et al. | 128/207.14 |
| 6,003,511 A | 12/1999 | Fukunaga et al. | 128/202.27 |
| 6,019,101 A | 2/2000 | Cotner et al. | 128/207.13 |
| 6,035,852 A | 3/2000 | Hoftman | 128/206.26 |
| 6,058,933 A | 5/2000 | Good et al. | 128/205.13 |
| D428,987 S | 8/2000 | Kwok | D24/110.1 |
| 6,112,746 A | 9/2000 | Kwok et al. | 128/207.13 |
| 6,123,071 A | 9/2000 | Berthon-Jones et al. | 128/204.18 |
| 6,129,082 A | 10/2000 | Leagre | 128/205.29 |
| 6,152,137 A | 11/2000 | Schwartz et al. | 128/846 |
| D435,650 S | 12/2000 | Kwok | D24/110.1 |
| 6,192,886 B1 | 2/2001 | Rudolph | 128/207.13 |
| 6,216,691 B1 | 4/2001 | Kenyon et al. | 128/205.18 |
| 6,263,874 B1 | 7/2001 | LeDez et al. | 128/206.21 |
| 6,342,040 B1 | 1/2002 | Starr et al. | 600/538 |
| 6,357,441 B1 | 3/2002 | Kwok et al. | 128/207.13 |
| 6,397,847 B1 | 6/2002 | Scarberry et al. | 128/206.24 |
| 6,401,713 B1 * | 6/2002 | Hill | A61M 16/00 128/204.18 |
| 6,412,487 B1 | 7/2002 | Gunaratnam et al. | 128/206.24 |
| 6,412,488 B1 | 7/2002 | Barnett et al. | 128/207.13 |
| 6,439,230 B1 | 8/2002 | Gunaratnam et al. | 128/206.21 |
| 6,439,231 B1 | 8/2002 | Fukunaga et al. | 128/207.14 |
| 6,446,288 B1 | 9/2002 | Pi | 5/636 |
| 6,459,923 B1 | 10/2002 | Plewes et al. | 600/411 |
| 6,463,931 B1 | 10/2002 | Kwok et al. | 128/207.11 |
| 6,467,483 B1 | 10/2002 | Kopacko et al. | 128/207.12 |
| D467,345 S | 12/2002 | Gingles et al. | D24/189 |
| 6,513,526 B2 | 2/2003 | Kwok et al. | 128/206.24 |
| 6,520,182 B1 | 2/2003 | Gunaratnam | 128/206.27 |
| 6,581,602 B2 | 6/2003 | Kwok et al. | 128/207.13 |
| 6,584,977 B1 | 7/2003 | Serowski | 128/206.24 |
| 6,612,306 B1 | 9/2003 | Mault | 128/204.22 |

(56) References Cited

U.S. PATENT DOCUMENTS

| | | | |
|---|---|---|---|
| 6,615,835 B1 * | 9/2003 | Cise | A61M 16/0463 128/200.26 |
| 6,626,178 B2 | 9/2003 | Morgan et al. | 128/206.26 |
| 6,631,713 B1 * | 10/2003 | Christopher | A61M 16/0488 128/200.21 |
| 6,631,718 B1 | 10/2003 | Lovell | 128/206.24 |
| 6,634,358 B2 | 10/2003 | Kwok et al. | 128/205.25 |
| 6,651,663 B2 | 11/2003 | Barnett et al. | 128/207.13 |
| 6,694,973 B1 | 2/2004 | Dunhao et al. | 128/203.12 |
| 6,701,927 B2 | 3/2004 | Kwok et al. | 128/207.13 |
| 6,729,333 B2 | 5/2004 | Barnett et al. | 128/207.13 |
| 6,736,139 B1 | 5/2004 | Wix | 128/206.21 |
| D493,523 S | 7/2004 | Barnett et al. | D24/110.4 |
| 6,779,524 B2 | 8/2004 | Strawder et al. | 128/206.21 |
| 6,792,943 B2 | 9/2004 | Kumar et al. | 128/200.26 |
| 6,796,308 B2 | 9/2004 | Gunaratnam et al. | 128/206.24 |
| 6,805,117 B1 | 10/2004 | Ho et al. | 128/201.22 |
| 6,832,610 B2 | 12/2004 | Gradon et al. | 128/206.27 |
| 6,863,071 B2 | 3/2005 | Annett et al. | 128/849 |
| 6,871,649 B2 | 3/2005 | Kwok et al. | 128/206.24 |
| 6,892,729 B2 | 5/2005 | Smith et al. | 128/204.18 |
| 6,895,965 B2 | 5/2005 | Scarberry et al. | 128/206.24 |
| 6,931,664 B1 | 8/2005 | Chen | 2/9 |
| 6,935,337 B2 | 8/2005 | Virr et al. | 128/203.16 |
| 6,981,503 B1 | 1/2006 | Shapiro | 128/845 |
| 7,004,168 B2 | 2/2006 | Mace et al. | 128/206.21 |
| 7,007,696 B2 | 3/2006 | Palkon et al. | 128/207.13 |
| 7,013,896 B2 | 3/2006 | Schmidt | 128/206.15 |
| 7,017,576 B2 | 3/2006 | Olsen et al. | 128/205.25 |
| 7,021,311 B2 | 4/2006 | Gunaratnam et al. | 128/206.24 |
| 7,028,981 B2 | 4/2006 | Horton | |
| 7,036,508 B2 | 5/2006 | Kwok | 128/207.11 |
| 7,047,971 B2 | 5/2006 | Ho et al. | 128/207.11 |
| 7,066,179 B2 | 6/2006 | Eaton et al. | 128/206.27 |
| 7,069,932 B2 | 7/2006 | Eaton et al. | 128/206.24 |
| 7,069,933 B2 | 7/2006 | Kwok et al. | 128/206.24 |
| 7,114,498 B1 | 10/2006 | Nashed | 128/205.27 |
| 7,159,587 B2 | 1/2007 | Drew et al. | 128/204.18 |
| 7,178,524 B2 | 2/2007 | Noble | 128/206.11 |
| 7,178,527 B2 | 2/2007 | Kwok et al. | 128/207.13 |
| 7,210,481 B2 | 5/2007 | Lovell et al. | 128/205.25 |
| 7,219,669 B1 | 5/2007 | Lovell et al. | 128/206.24 |
| 7,237,551 B2 | 7/2007 | Ho et al. | 128/207.13 |
| 7,243,651 B2 | 7/2007 | Kwok et al. | 128/205.25 |
| 7,287,528 B2 | 10/2007 | Ho et al. | 128/206.21 |
| 7,341,060 B2 | 3/2008 | Ging et al. | 128/206.11 |
| 7,383,839 B2 | 6/2008 | Porat et al. | 128/207.18 |
| 7,445,602 B2 | 11/2008 | Yamamori | 128/201.27 |
| 7,448,386 B2 | 11/2008 | Ho et al. | 128/206.21 |
| 7,467,431 B2 | 12/2008 | Weedling et al. | 5/633 |
| 7,487,772 B2 | 2/2009 | Ging et al. | 128/202.27 |
| 7,487,777 B2 | 2/2009 | Gunaratnam et al. | 128/206.24 |
| 7,500,280 B2 | 3/2009 | Dixon et al. | 5/713 |
| 7,500,482 B2 | 3/2009 | Biederman | 128/206.21 |
| 7,614,398 B2 | 11/2009 | Virr et al. | 128/203.26 |
| 7,631,644 B2 | 12/2009 | Ho et al. | 128/206.21 |
| 7,665,464 B2 | 2/2010 | Kopacko et al. | 128/206.24 |
| 7,669,599 B2 | 3/2010 | Gunaratnam et al. | 128/205.25 |
| 7,700,129 B2 | 4/2010 | Ito et al. | 424/486 |
| 7,743,767 B2 | 6/2010 | Ging et al. | 128/206.24 |
| 7,753,051 B2 | 7/2010 | Burrow et al. | 128/207.11 |
| 7,779,832 B1 | 8/2010 | Ho | 128/201.22 |
| 7,841,988 B2 | 11/2010 | Yamamori | 600/532 |
| 7,870,859 B2 | 1/2011 | Barnett et al. | 128/204.24 |
| 7,874,292 B2 | 1/2011 | Smith et al. | 128/206.27 |
| 7,913,337 B1 | 3/2011 | Masson | 5/618 |
| 7,926,487 B2 | 4/2011 | Drew et al. | 128/205.25 |
| 7,927,285 B2 | 4/2011 | Yamamori | 600/532 |
| 7,931,024 B2 | 4/2011 | Ho et al. | 128/206.21 |
| 7,938,117 B2 | 5/2011 | Chiesa et al. | 128/205.25 |
| 7,950,392 B2 | 5/2011 | Kwok et al. | 128/206.24 |
| 7,975,694 B2 | 7/2011 | Ho | 128/205.25 |
| 7,997,267 B2 | 8/2011 | Ging et al. | 128/202.27 |
| 8,001,968 B2 | 8/2011 | Doty et al. | 128/205.27 |
| 8,001,970 B2 | 8/2011 | King et al. | 128/845 |
| 8,028,699 B2 | 10/2011 | Ho et al. | 128/206.21 |
| 8,042,539 B2 | 10/2011 | Chandran et al. | 128/206.28 |
| 8,042,541 B2 | 10/2011 | Amarasinghe et al. | 128/206.27 |
| 8,056,561 B2 | 11/2011 | Kwok et al. | 128/206.24 |
| 8,132,270 B2 | 3/2012 | Lang et al. | 2/422 |
| 8,161,971 B2 | 4/2012 | Jaffe | 128/200.24 |
| 8,191,553 B2 | 6/2012 | Haworth et al. | 128/845 |
| 8,210,181 B2 | 7/2012 | Gunaratnam et al. | 128/207.11 |
| 8,261,745 B2 | 9/2012 | Chandran et al. | 128/206.24 |
| 8,261,746 B2 | 9/2012 | Lynch et al. | 128/206.24 |
| 8,267,091 B2 | 9/2012 | Smith et al. | 128/202.27 |
| 8,302,224 B2 | 11/2012 | Lehman | 5/486 |
| 8,312,883 B2 | 11/2012 | Gunaratnam et al. | 128/207.18 |
| 8,336,142 B1 | 12/2012 | See et al. | 5/634 |
| 8,336,549 B2 | 12/2012 | Nashed | 128/206.28 |
| 8,347,889 B2 | 1/2013 | Farnum | 128/845 |
| 8,365,734 B1 | 2/2013 | Lehman | 128/206.28 |
| 8,397,724 B2 | 3/2013 | Sher et al. | 128/205.25 |
| D681,383 S | 5/2013 | Derman et al. | D6/603 |
| 8,443,807 B2 | 5/2013 | McAuley et al. | 128/207.18 |
| 8,485,190 B2 | 7/2013 | Barnett et al. | 128/206.24 |
| 8,485,192 B2 | 7/2013 | Davidson et al. | 128/206.24 |
| 8,490,623 B2 | 7/2013 | Berthon-Jones et al. | 128/206.21 |
| RE44,453 E | 8/2013 | Virr et al. | 128/203.27 |
| 8,479,726 B2 | 9/2013 | McAuley | 28/201.17 |
| 8,522,783 B2 | 9/2013 | Kwok et al. | 128/204.26 |
| 8,528,558 B2 | 9/2013 | Drew et al. | 128/205.25 |
| 8,550,081 B2 | 10/2013 | Davidson et al. | 128/206.24 |
| 8,550,082 B2 | 10/2013 | Davidson et al. | 128/206.24 |
| 8,550,083 B2 | 10/2013 | Davidson et al. | 128/206.24 |
| 8,555,885 B2 | 10/2013 | Davidson et al. | 128/206.24 |
| 8,567,402 B2 | 10/2013 | Gunaratnam et al. | 128/205.25 |
| 8,567,404 B2 | 10/2013 | Davidson et al. | 128/206.24 |
| D693,603 S | 11/2013 | Esquivel et al. | D6/602 |
| 8,573,211 B2 | 11/2013 | Ho et al. | 128/206.24 |
| 8,573,212 B2 | 11/2013 | Lynch et al. | 128/206.24 |
| 8,573,213 B2 | 11/2013 | Davidson et al. | 128/206.24 |
| 8,573,214 B2 | 11/2013 | Davidson et al. | 128/206.24 |
| 8,573,215 B2 | 11/2013 | Davidson et al. | 128/206.24 |
| 8,573,217 B2 | 11/2013 | Todd et al. | 128/207.12 |
| 8,578,935 B2 | 11/2013 | Davidson et al. | 128/206.24 |
| 8,578,939 B1 | 11/2013 | Kimani Mwangi et al. | 128/848 |
| 8,613,280 B2 | 12/2013 | Davidson et al. | 128/206.24 |
| 8,613,281 B2 | 12/2013 | Davidson et al. | 128/206.24 |
| 8,616,211 B2 | 12/2013 | Davidson et al. | 128/206.24 |
| 8,631,792 B2 | 1/2014 | Ho et al. | 128/206.24 |
| 8,636,006 B2 | 1/2014 | Kwok et al. | 128/207.13 |
| 8,667,965 B2 | 3/2014 | Gunaratnam et al. | 128/207.13 |
| 8,684,004 B2 | 4/2014 | Eifler | 128/206.24 |
| 8,689,366 B2 | 4/2014 | Ho | 2/452 |
| 8,707,950 B1 | 4/2014 | Rubin | 128/202.27 |
| 8,714,157 B2 | 5/2014 | McAuley et al. | 128/205.25 |
| 8,752,551 B2 | 6/2014 | Chandran et al. | 128/206.28 |
| 8,807,134 B2 | 8/2014 | Ho et al. | 128/206.21 |
| 8,807,135 B2 | 8/2014 | Worboys et al. | 128/206.24 |
| 8,813,748 B2 | 8/2014 | Kwok et al. | 128/206.24 |
| 8,881,728 B2 | 11/2014 | Sher et al. | 128/205.25 |
| 8,915,861 B2 | 12/2014 | Yamamori et al. | 600/532 |
| 8,939,151 B2 | 1/2015 | McAuley et al. | 128/205.25 |
| 8,944,061 B2 | 2/2015 | D'Souza et al. | 128/206.24 |
| D726,303 S | 4/2015 | Rollins | D24/110.1 |
| 9,010,330 B2 | 4/2015 | Barlow et al. | 128/201.18 |
| 9,010,331 B2 | 4/2015 | Lang et al. | A61M 16/06 |
| 9,022,029 B2 | 5/2015 | Varga et al. | A61B 5/0836 |
| 9,027,556 B2 | 5/2015 | Ng et al. | 128/205.25 |
| 9,138,169 B2 | 9/2015 | Beard | A61B 5/097 |
| 9,186,474 B1 | 11/2015 | Rollins | |
| 9,295,799 B2 | 3/2016 | McAuley et al. | A61M 16/06 |
| 9,295,800 B2 | 3/2016 | Davidson et al. | A61M 16/06 |
| D753,287 S | 4/2016 | Darab | D24/110.4 |
| D753,816 S | 4/2016 | Darab | D24/110.4 |
| 9,375,545 B2 | 6/2016 | Darkin et al. | A61M 16/0683 |
| 2002/0074001 A1 | 6/2002 | Kwok et al. | |
| 2002/0174868 A1 | 11/2002 | Kwok et al. | 128/205.25 |
| 2003/0024533 A1 | 2/2003 | Sniadach | 128/205.25 |
| 2003/0145859 A1 | 8/2003 | Bohn et al. | 128/206.24 |

(56) References Cited

U.S. PATENT DOCUMENTS

| | | | |
|---|---|---|---|
| 2003/0183232 A1 | 10/2003 | Fukunaga et al. | 128/204.18 |
| 2004/0069306 A1 | 4/2004 | Moenning | 128/207.13 |
| 2004/0221850 A1 | 11/2004 | Ging et al. | 128/206.27 |
| 2005/0028811 A1 | 2/2005 | Nelson et al. | 128/200.11 |
| 2005/0145247 A1 | 7/2005 | Nashed | 128/204.18 |
| 2005/0160532 A1 | 7/2005 | Froelich | 5/637 |
| 2005/0193493 A1 | 9/2005 | Gabbay | 5/644 |
| 2006/0032500 A1 | 2/2006 | Ghiron et al. | 128/202.27 |
| 2006/0042631 A1 | 3/2006 | Martin et al. | 128/207.18 |
| 2006/0118117 A1 | 6/2006 | Berthon-Jones et al. 128/206.21 |
| 2006/0124131 A1 | 6/2006 | Chandran et al. | |
| 2006/0168730 A1 | 8/2006 | Menkedick et al. | 5/618 |
| 2006/0174889 A1 | 8/2006 | Noble | 128/206.11 |
| 2006/0231091 A1 | 10/2006 | Camarillo | 128/200.21 |
| 2007/0062536 A1 | 3/2007 | McAuley et al. | 128/206.21 |
| 2007/0113847 A1 | 5/2007 | Acker et al. | 128/204.18 |
| 2007/0113856 A1 | 5/2007 | Acker et al. | 128/207.14 |
| 2007/0267017 A1 | 11/2007 | McAuley et al. | 128/204.18 |
| 2007/0271699 A1 | 11/2007 | Sacchetti | 5/495 |
| 2007/0295335 A1 | 12/2007 | Nashed | 128/206.24 |
| 2008/0053446 A1 | 3/2008 | Sleeper et al. | 128/205.25 |
| 2008/0092898 A1 | 4/2008 | Schneider et al. | 128/206.28 |
| 2008/0196715 A1 | 8/2008 | Yamamori | 128/203.12 |
| 2008/0221470 A1 | 9/2008 | Sather et al. | 600/533 |
| 2008/0230067 A1 | 9/2008 | Kwok et al. | 128/206.24 |
| 2009/0084385 A1 | 4/2009 | Lang | 128/206.21 |
| 2009/0114229 A1 | 5/2009 | Frater et al. | 128/206.24 |
| 2009/0114230 A1 | 5/2009 | Hernandez et al. | 128/206.24 |
| 2009/0133696 A1 | 5/2009 | Remmers et al. | 128/204.26 |
| 2009/0159084 A1 | 6/2009 | Sher et al. | |
| 2009/0178680 A1 | 7/2009 | Chang | 128/206.27 |
| 2009/0250061 A1 | 10/2009 | Marasigan | 128/205.13 |
| 2009/0260628 A1 | 10/2009 | Flynn | 128/203.28 |
| 2009/0301472 A1 | 12/2009 | Kim | 128/200.16 |
| 2009/0320850 A1 | 12/2009 | Wallnewitz et al. | 128/207.11 |
| 2010/0122701 A1 | 5/2010 | Gunaratnam et al. | |
| 2010/0122705 A1 | 5/2010 | Moenning, Jr. | |
| 2010/0147313 A1 | 6/2010 | Albrecht | 128/845 |
| 2010/0170513 A1* | 7/2010 | Bowditch | A61M 16/00 128/204.23 |
| 2010/0170516 A1 | 7/2010 | Grane | |
| 2010/0218316 A1 | 9/2010 | Nissen et al. | 5/632 |
| 2010/0224199 A1 | 9/2010 | Smith et al. | 128/863 |
| 2010/0275919 A1 | 11/2010 | Sung | 128/204.22 |
| 2010/0313891 A1 | 12/2010 | Veliss et al. | |
| 2011/0054366 A1 | 3/2011 | Smith et al. | 601/15 |
| 2011/0072582 A1 | 3/2011 | Patterson et al. | 5/484 |
| 2011/0083670 A1 | 4/2011 | Walacavage | 128/205.12 |
| 2011/0092930 A1 | 4/2011 | Poorman | 604/356 |
| 2011/0108035 A1 | 5/2011 | Samaniego | 128/206.17 |
| 2011/0114099 A1 | 5/2011 | Goldstein | 128/848 |
| 2011/0155136 A1 | 6/2011 | Lee | 128/205.24 |
| 2011/0173750 A1 | 7/2011 | Lehmann | 5/486 |
| 2011/0186076 A1 | 8/2011 | Daly | 128/204.23 |
| 2011/0214674 A1 | 9/2011 | Ging et al. | 128/206.21 |
| 2011/0253150 A1 | 10/2011 | King | 128/845 |
| 2011/0265796 A1 | 11/2011 | Amarasinghe et al. 128/206.28 |
| 2011/0290253 A1 | 12/2011 | McAuley et al. | 128/205.25 |
| 2011/0315143 A1 | 12/2011 | Frater | |
| 2012/0080035 A1 | 4/2012 | Guney et al. | 128/205.25 |
| 2012/0111330 A1 | 5/2012 | Gartner | 128/205.23 |
| 2012/0144588 A1 | 6/2012 | Heimbrock et al. | 5/624 |
| 2012/0180220 A1 | 7/2012 | Popitz | 5/638 |
| 2012/0222680 A1 | 9/2012 | Eves | |
| 2012/0227736 A1 | 9/2012 | Bowsher | 128/202.27 |
| 2012/0234326 A1 | 9/2012 | Mazzone | |
| 2012/0247475 A1 | 10/2012 | Hernandez et al. | |
| 2012/0285455 A1 | 11/2012 | Varga et al. | 128/204.21 |
| 2012/0285466 A1 | 11/2012 | Pierro et al. | 128/206.24 |
| 2012/0305001 A1 | 12/2012 | Tatkov | |
| 2013/0014760 A1 | 1/2013 | Matula, Jr. et al. | 128/205.25 |
| 2013/0019870 A1 | 1/2013 | Collazo et al. | |
| 2013/0023729 A1 | 1/2013 | Vazales | |
| 2013/0060157 A1* | 3/2013 | Beard | A61M 16/06 600/532 |
| 2013/0109992 A1 | 5/2013 | Guyette | 600/532 |
| 2013/0146060 A1 | 6/2013 | Ho et al. | 128/205.25 |
| 2013/0186413 A1 | 7/2013 | Haines et al. | 128/854 |
| 2013/0190643 A1 | 7/2013 | Brambilla | A61M 16/00875 |
| 2013/0192601 A1 | 8/2013 | Reischl et al. | 128/205.25 |
| 2013/0192602 A1 | 8/2013 | Leibitzki et al. | 128/205.27 |
| 2013/0199537 A1 | 8/2013 | Formica et al. | A61M 16/0666 |
| 2013/0319417 A1 | 12/2013 | Weinman | 128/205.25 |
| 2014/0076311 A1 | 3/2014 | Darab | 128/203.12 |
| 2014/0083425 A1 | 3/2014 | Moenning | 128/203.29 |
| 2014/0144448 A1 | 5/2014 | Eifler | 128/206.24 |
| 2014/0158135 A1 | 6/2014 | Shyong | 128/206.21 |
| 2014/0158136 A1 | 6/2014 | Romagnoli et al. | 128/206.24 |
| 2014/0215687 A1 | 8/2014 | Andrews | 2/170 |
| 2014/0243600 A1 | 8/2014 | Eisenberger | 600/114 |
| 2014/0245537 A1 | 9/2014 | Allen | 5/622 |
| 2014/0251333 A1 | 9/2014 | Burk | 128/205.12 |
| 2014/0326246 A1 | 11/2014 | Chodkowski et al. | 128/206.24 |
| 2014/0352072 A1 | 12/2014 | Holladay | 5/655.5 |
| 2014/0360504 A1 | 12/2014 | Kwok | A61M 16/0605 |
| 2015/0047647 A1 | 2/2015 | Winer | 128/854 |
| 2015/0059759 A1 | 3/2015 | Frater et al. | 128/205.25 |
| 2015/0144140 A1 | 5/2015 | Eury | A61M 16/0622 |
| 2015/0217075 A1 | 8/2015 | Nair | 600/531 |
| 2015/0238716 A1 | 8/2015 | Budhiraja et al. | A61M 16/0003 |
| 2015/0250970 A1 | 9/2015 | Bowsher | A61M 16/0616 |
| 2015/0250971 A1 | 9/2015 | Bachelder et al. | A61M 16/0616 |
| 2015/0273170 A1 | 10/2015 | Bachelder et al. | A61M 16/0616 |
| 2015/0273171 A1 | 10/2015 | Sullivan et al. | A61M 16/0683 |
| 2015/0335852 A1 | 11/2015 | Miller | A61M 16/208 |
| 2016/0015923 A1 | 1/2016 | Chodkowski et al. | A61M 16/0622 |
| 2016/0022944 A1 | 1/2016 | Chodkowski et al. | A61M 16/0616 |
| 2016/0038709 A1 | 2/2016 | Beard | 128/205.12 |
| 2016/0067441 A1 | 3/2016 | Bearne et al. | A61M 16/0683 |
| 2016/0184540 A1 | 6/2016 | Kokko | A61M 16/0069 |
| 2016/0213871 A1 | 7/2016 | Darab | |
| 2016/0279368 A1 | 9/2016 | Isenberg | A61M 16/0605 |

FOREIGN PATENT DOCUMENTS

| | | | |
|---|---|---|---|
| CN | 103153378 A | 6/2013 | |
| DE | 19947722 | 4/2001 | A61M 16/06 |
| EP | 2433666 | 3/2012 | A61M 16/06 |
| GB | 187863 | 11/1922 | |
| GB | 2209950 A | 6/1989 | |
| GB | 2456136 | 7/2009 | |
| JP | H0294566 U | 7/1990 | |
| JP | H071155 Y2 | 1/1995 | |
| JP | 2005318975 A | 11/2005 | |
| JP | 2008511399 A | 4/2008 | |
| WO | WO2010059592 | 5/2010 | A61M 16/06 |
| WO | WO-2012106373 A2 | 8/2012 | |
| WO | WO2013036839 | 3/2013 | A61M 16/06 |
| WO | WO2013/064950 | 5/2013 | |
| WO | WO-2013142909 A1 | 10/2013 | |
| WO | WO2014038959 | 3/2014 | A61M 16/00 |
| WO | WO-2014077708 A1 | 5/2014 | |
| WO | WO2014210606 | 12/2014 | A61G 13/02 |
| WO | WO2015063283 | 5/2015 | A61M 16/06 |
| WO | WO2015131262 | 9/2015 | A61M 16/06 |
| WO | WO2015147947 | 10/2015 | A61M 15/06 |
| WO | WO 2015/187995 | 12/2015 | A61M 16/06 |
| WO | WO2016007749 | 1/2016 | A61M 16/10 |
| WO | WO2016097948 | 6/2016 | A61M 16/06 |

OTHER PUBLICATIONS

Japanese Office Action (w/translation) issued in application No. 2016-006559, dated Aug. 29, 2016 (3 pgs).

(56) References Cited

OTHER PUBLICATIONS

Japanese Office Action (w/translation) issued in application No. 2016-006560, dated Aug. 29, 2016 (3 pgs).
Australian Certificate of Registration issued in application No. 201512961, dated Aug. 10, 2015 (5 pgs).
Australian Certificate of Registration issued in application No. 201512962, dated Aug. 12, 2015 (5 pgs).
Ball et al., "Performance comparison of two anaesthetic facemasks," Anaesth Intensive Care, Apr. 2007, vol. 35, issue 2, 226-9 (abstract only) (2 pgs).
Canadian Office Action issued in application No. 162891, dated Apr. 5, 2016 (1 pg).
Canadian Office Action issued in application No. 162891, dated Nov. 10, 2015 (7 pgs).
CPAP product description, http://www.cpap.com/productpage/pr-amara-full-face-cpap-mask-gel-silicone.html, downloaded Jul. 28, 2016. 11 pages.
CPAPXCHANGE product image, http://www.cpapxchange.com/cpap-masks-bipap-masks/bluegel-full-cushion-comfortgel-cpap-bipap-masks.jpg, downloaded Jul. 28, 2016, 1 page.
DirectHome Medical product description, http://www.directhomemedical.com/profilelite-gel-cpap-mask-philipsrespironics.html#.VwXLIPkrLIU, downloaded Jul. 28, 2016, 6 pages.
Indian Office Action issued in related Indian Design Patent Application Serial No. 272704, dated Aug. 28, 2015 (13 pgs).
InnoMed Technologies Hybrid mask product description, http://innomedinc.com/hybrid/, downloaded Jul. 28, 2016,4 pages.
InnoMed Technologies Sylent mask product description, http://innomedinc.com/sylent-ne-disposable-nasal-mask/, downloaded Jul. 28, 2016, 2 pages.
International Preliminary Report on Patentability issued in application No. PCT/US14/44934, dated Jan. 7, 2016 (12 pgs).
International Preliminary Report on Patentability issued in application No. PCT/US2105/021323, dated Oct. 6, 2016 (8 pgs).
International Search Report and Written Opinion issued in application No. PCT/US2015/044341, dated Jan. 7, 2016 (13 pgs).
International Search Report and Written Opinion issued in application No. PCT/US2015/34277, dated Nov. 23, 2015 (17 pgs).
International Search Report issued in application No. PCT/US14/44934, dated Jan. 2, 2015 (16 pgs).
Invitation to Pay Additional Fees issued in application No. PCT/US15/44341, dated Oct. 21, 2015 (2 pgs).
Invitation to Pay Additional Fees issued in application No. PCT/US14/44934, dated Oct. 24, 2014 (3 pgs).
Israeli Notice of Allowance issued in application No. 57056 (no. translation), dated May 29, 2016 (1 pg).
Israeli Office Action issued in application No. 57056 (w/translation of relevant portions), dated Nov. 1, 2015 (3 pgs).
Israeli Office Action issued in application No. 57850 (w/translation of relevant portions), dated Feb. 15, 2016 (3 pgs).
Israeli Office Action issued in application No. 57850 (w/translation of relevant portions), dated Jun. 30, 2016 , (2 pgs).
Israeli Office Action issued in application No. 57850 (w/translation of relevant portions), dated Jul. 19, 2016 (3 pgs).
Japanese Office Action issued in application No. 2015-013148, dated Dec. 4, 2015 (3 pgs).
Japanese Office Action issued in application No. 2016-005262, dated Jun. 30, 2016 (1 pg).
Japanese Office Action issued in application No. 2016-005263, dated Jun. 30, 2016 (1 pg).
Korean Design of Registration issued in Korean related Application Serial No. 30-2015-0029561, M001 (w/translation), dated Jun. 29, 2016 (3 pgs).
Korean Design of Registration issued in Korean related Application Serial No. 30-2015-0029561, M002 (w/translation), dated Jun. 27, 2016 (3 pgs).
Korean Office Action issued in application No. 30-2015-0029561, M002 (w/translation), dated May 23, 2016 (6 pgs).
Korean Office Action issued in application No. 30-2015-0029561, M001, dated May 23, 2016 (2 pgs).
Korean Office Action issued in application No. 30-2015-0029561, M002 (w/translation), dated Dec. 24, 2015 (7 pgs).
Korean Office Action issued in application No. 30-2015-0029561, M001 (w/translation), dated Dec. 24, 2015 (12 pgs).
Korean Office Action issued in application No. 30/2015-0029561, M001, dated Jun. 9, 2016 (16 pgs).
Korean Office Action issued in application No. 30-2015-0029561, M002, dated Jun. 9, 2016 (3 pgs).
Liang, Yafen et al., "Nasal Ventilation is More Effective than Combined Oral-Nasal Ventilation during Induction of General Anesthesia in Adult Subjects", Anesthesiology 2008, vol. 108, No. 6, Jun. 2008, pp. 998-1003.
Office Action issued in U.S. Appl. No. 29/530,124, dated Aug. 12, 2016 (17 pgs).
Office Action issued in related Design U.S. Appl. No. 29/520,420, dated Aug. 11, 2016 (18 pgs).
Sleep Medicine Solutions product description, http://sleepmedicinesolutions.net.au/cpap-spare-parts/26-fisher-paykel-zest-foams.html, downloaded Jul. 28, 2016, 2 pages.
Sleepnet homepage, https://web.archive.org/web/20111031122613/http://www.sleepnetmasks.com/, downloaded Jul. 28, 2016, 4 pages.
U.S. Appl. No. 15/288,973, filed Oct. 7, 2016, Pedro et al.
European Supplementary Partial European Search Report for application No. 14818563.0, dated Jan. 30, 2017 (6 pages).
Notice of Allowance issued in U.S. Appl. No. 15/288,973, dated Feb. 1, 2017 (25 pgs).
Notice of Decision of Registration for Design issued in Korean Design Application 30-20016-0014111, dated Dec. 13, 2016 (3 pages with translation).
Office Action Issued in U.S. Appl. No. 15/272,160, dated Jan. 4, 2017 (31 pgs).
Office Action issued in U.S. Appl. No. 15/288,973, dated Dec. 14, 2016 (21 pgs).
Preliminary Report on Patentability issued in application No. PCT/US2015/034277, dated Dec. 15, 2016 (11 pgs).
Singapore Search Report issued in application 11201510589, dated Jan. 31, 2017 (11 pgs).
Advisory Action issued in related U.S. Appl. No. 29/530,124 dated Apr. 19, 2017 (6 pgs).
Advisory Action issued in related U.S. Appl. No. 29/520,420 dated Apr. 7, 2017 (3 pgs).
Office Action issued in related U.S. Appl. No. 15/272,074 dated Apr. 19, 2017 (54 pgs).
Office Action issued in U.S. Appl. No. 15/272,160, dated Apr. 24, 2017 (39 pgs).
International Preliminary Report on Patentability issued in application No. PCT/US2015/044341, dated Mar. 2, 2017 (10 pgs).
Office Action issued in U.S. Appl. No. 29/520,420, dated Feb. 24, 2017 (14 pgs).
Office Action issued in U.S. Appl. No. 29/530,124, dated Feb. 28, 2017 (16 pgs).
Chinese First Office Action issued in application No. 201480042735.9 dated Apr. 5, 2017 (w/ translation) (18 pgs).
Extended European Search Report issued in application No. 14818563.0-1651 dated May 3, 2017 (12 pgs).
Japanese Decision for Registration issued in application on. 2016-006559, dated May 12, 2017 (w/ translation) (2 pgs).
Japanese Decision for Registration issued in application on. 2016-006560, dated May 12, 2017 (w/ translation) (2 pgs).
Japanese Office Action (w/translation) issued in application 2016-005263, dated Apr. 28, 2017 (8 pgs).
Japanese Office Action (w/translation) issued in application 2016-005262, dated Apr. 28, 2017 (7 pgs).
Office Action issued in application No. 29/520,420, dated Jun. 15, 2017 (12 pgs).
Office Action issued in U.S. Appl. No. 29/520,420, dated Jun. 15, 2017 (12 pgs).
Office Action issued in U.S. Appl. No. 29/530,124, dated Jun. 21, 2017 (14 pgs).
U.S. Appl. No. 29/511,716, filed Dec. 12, 2014.
U.S. Appl. No. 29/520,420, filed Mar. 13, 2015.
U.S. Appl. No. 29/530,124, filed Jun. 12, 2015.
U.S. Appl. No. 14/901,647, filed Dec. 28, 2015.

(56) References Cited

OTHER PUBLICATIONS

U.S. Appl. No. 15/217,753, filed Jul. 22, 2016.
U.S. Appl. No. 15/127,758, filed Sep. 20, 2016.
U.S. Appl. No. 15/127,759, filed Sep. 20, 2016.
U.S. Appl. No. 15/127,760, filed Sep. 20, 2016.
U.S. Appl. No. 15/272,074, filed Sep. 21, 2016.
U.S. Appl. No. 15/272,160, filed Sep. 21, 2016.
U.S. Appl. No. 15/288,973, filed Oct. 7, 2016.
U.S. Appl. No. 15/510,469, filed Mar. 10, 2017.
U.S. Appl. No. 29/520,420, filed Mar. 13, 2015, Reilly et al.
U.S. Appl. No. 29/530,124, filed Jun. 12, 2015, Reilly et al.
U.S. Appl. No. 14/901,647, filed Dec. 28, 2015, Pedro et al.
U.S. Appl. No. 15/217,753, filed Jul. 22, 2016, Pedro et al.
U.S. Appl. No. 15/127,758, filed Sep. 20, 2016, Pedro et al.
U.S. Appl. No. 15/127,759, filed Sep. 20, 2016, Pedro et al.
U.S. Appl. No. 15/127,760, filed Sep. 20, 2016, Pedro et al.
U.S. Appl. No. 15/272,074, filed Sep. 21, 2016, Pedro et al.
U.S. Appl. No. 15/272,160, filed Sep. 21, 2016, Pedro et al.
U.S. Appl. No. 15/510,469, filed Mar. 10, 2017, Reilly et al.
Chinese First Notification to Make Rectification issued in application No. 201730161613.8, dated Aug. 7, 2017 (2 pgs).
Chinese Notification of Grant issued in application No. 201530191921.6, dated Feb. 15, 2016 (12 pgs).
Chinese Second Notification to Make Rectification issued in application No. 201730161613.8, dated Sep. 19, 2017 (11 pgs).
Chinese Second Office Action issued in application No. 201480042735.9, dated Nov. 6, 2017 (21 pgs).
European Examination Report issued in application 003933217-0001, dated May 16, 2017 (2 pgs).
International Preliminary Report on Patentability issued in application No. PCT/US2016/037070, dated Dec. 12, 2017 (7 pgs).
International Search Report and Written Opinion issued in application No. PCT/US2017/048046, dated Nov. 6, 2017 (11 pgs).
Japanese Certified Decision for Registration issued in application No. 2016-005262, dated Dec. 22, 2017 (4 pgs).
Japanese Certified Decision for Registration issued in application No. 2016-005263, dated Dec. 22, 2017 (4 pgs).
Japanese Decision for Registration issued in application No. 2017-009813, dated Oct. 6, 2017 (2 pgs).
Japanese Office Action issued in application No. 2017-009813, dated Jul. 20, 2017 (3 pgs).
Notice of Allowance (Corrected) issued in application No. 15/288,973, dated Mar. 10, 2017 (9 pgs).
Notice of Allowance (Corrected) issued in application No. 15/288,973, dated Mar. 24, 2017 (9 pgs).
Notice of Allowance (Corrected) issued in application No. 15/288,973, dated Feb. 10, 2017 (16 pgs).
Office Action issued in application No. 15/272,074, dated Jul. 31, 2017 (34 pgs).
Office Action issued in application No. 15/272,074, dated Sep. 13, 2017 (5 pgs).
Office Action issued in application No. 15/272,160, dated Dec. 15, 2017 (34 pgs).
Office Action issued in application No. 29/520,420, dated Dec. 8, 2017 (5 pgs).
Office Action issued in application No. 29/530,124 dated Aug. 9, 2017 (11 pgs).
Office Action issued in application No. 29/530,124, dated Aug. 30, 2017 (3 pgs).
Office Action issued in application No. 29/530,124, dated Jun. 21, 2017 (14 pgs).
Office Action issued in application No. 29/530,124, dated Nov. 29, 2017 (31 pgs).
Singapore Invitation to Respond to Written Opinion issued in application No. 11201610048P, dated Sep. 19, 2017 (16 pgs).
Singapore Invitation to Respond to Written Opinion issued in application No. 11201701253U, dated Nov. 8, 2017 (12 pgs).
Chinese Office Action for Application No. 201580029981.5, dated Sep. 5, 2018, 14 pages.
Extended European Search Report for Application No. 15803670.7, dated Oct. 24, 2018, 12 pages.
Extended European Search Report for Application No. 15833101.7, dated Jul. 3, 2018, 13 pages.
Japanese Office Action for Application No. 2017-509724, dated Jul. 24, 2018, 7 pages.
Partial Supplementary European Search Report for Application No. 16808466.3, dated Jan. 22, 2019, 14 pages.
Australian Examination Report No. 1 for Application No. 2015269351, dated Mar. 8, 2019, 5 pages.
Chinese Office Action for Application No. 201580029981.5, dated Apr. 15, 2019, 12 pages.
Japanese Office Action for Application No. 2016-571111, dated Jun. 11, 2019, 10 pages.
Chinese Office Action for Application No. 201580029981.5, dated Oct. 8, 2019, 14 pages.

\* cited by examiner

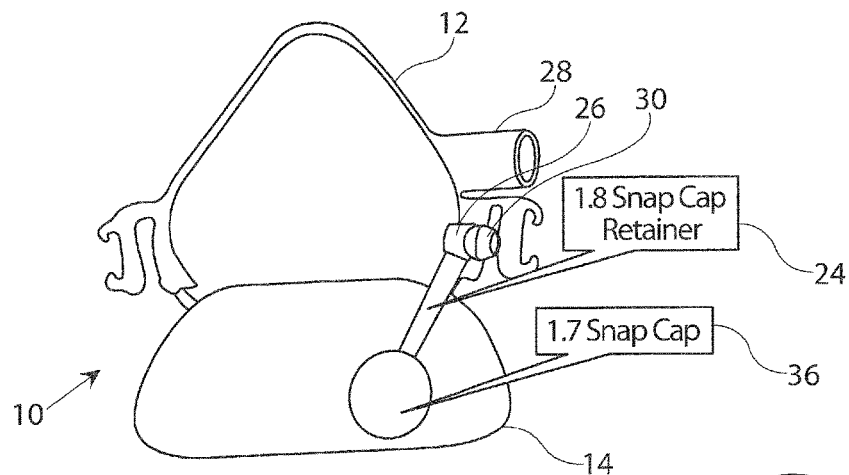
Figure 1
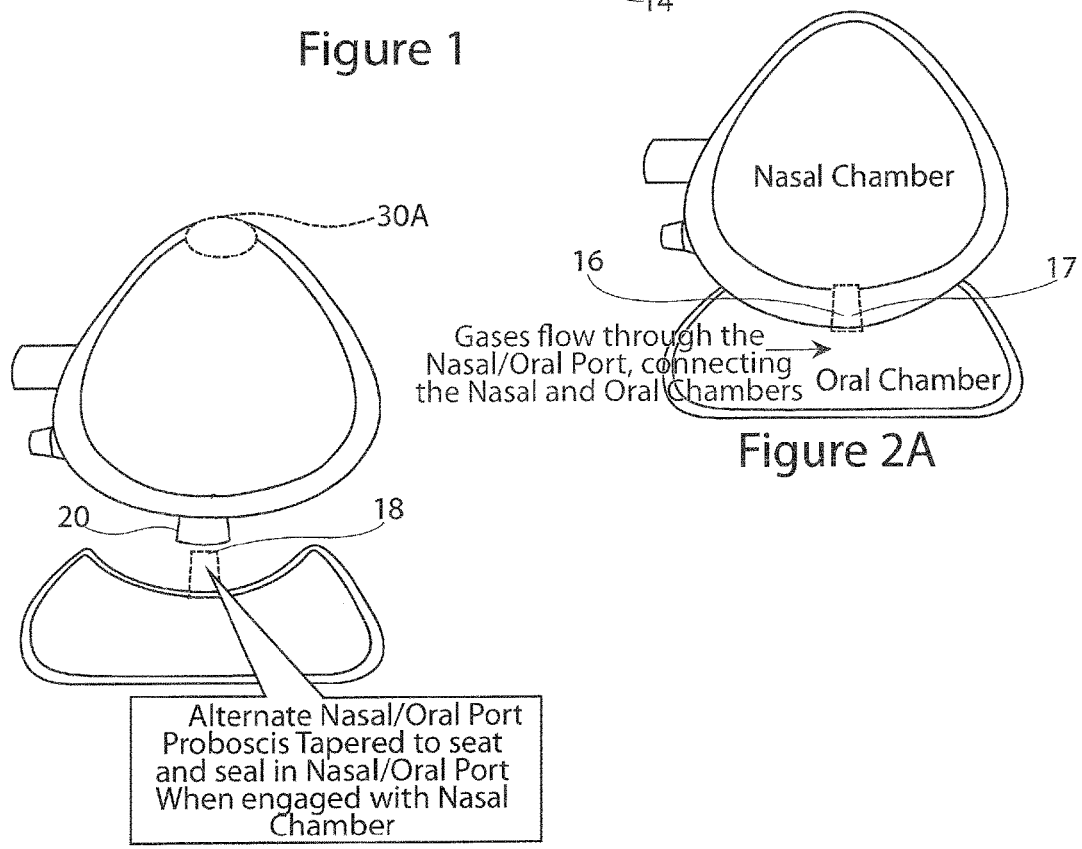
Figure 2A
Figure 3

Example of a Snap Cap
with a hinged Retainer

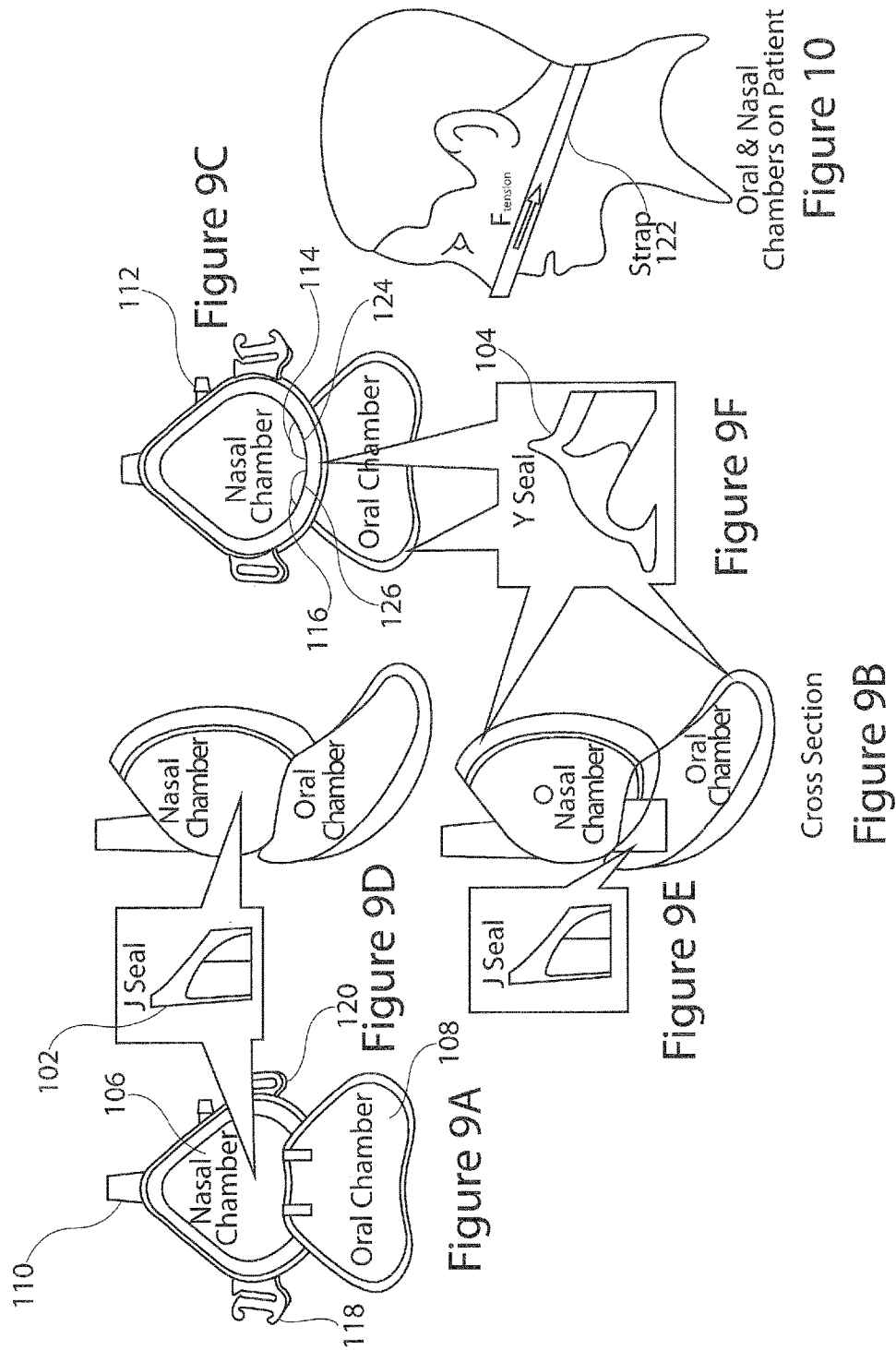

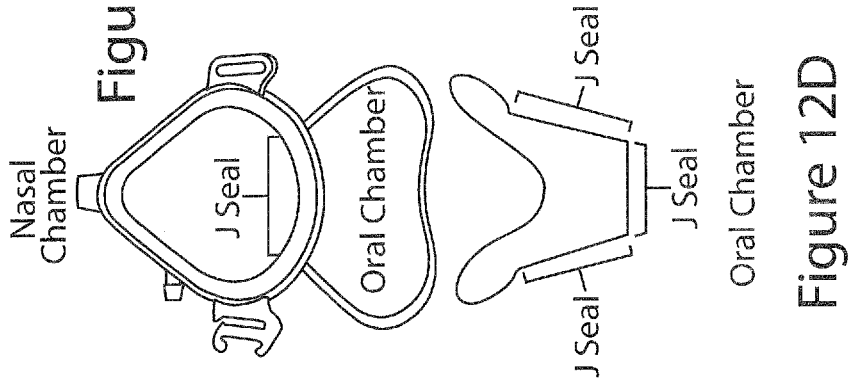
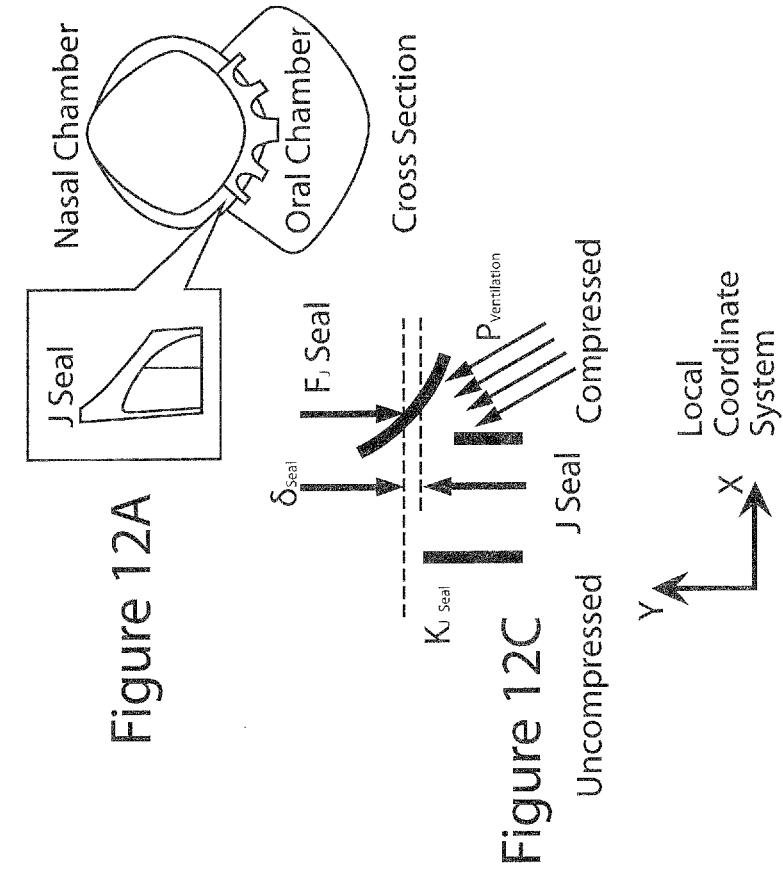

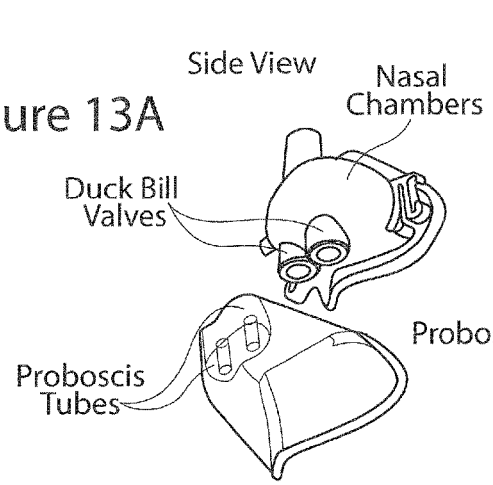
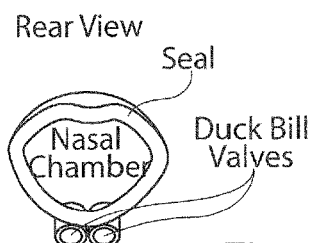
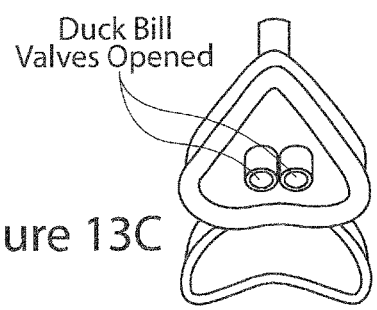
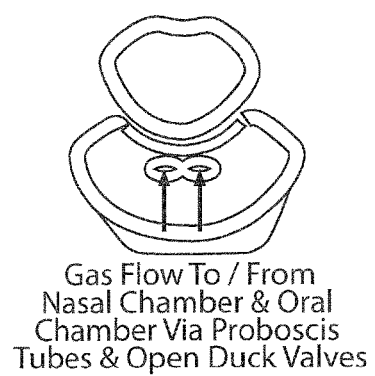
Figure 13A — Side View: Nasal Chambers, Duck Bill Valves, Proboscis Tubes
Figure 13B — Rear View: Seal, Nasal Chamber, Duck Bill Valves, Proboscis, Oral Chamber, Seal
Figure 13C — Duck Bill Valves Opened
Figure 13D — Proboscis Tube Openings
Figure 13E — Gas Flow To / From Nasal Chamber & Oral Chamber Via Proboscis Tubes & Open Duck Valves Side View Front View Gas Flow To/From
Nasal Chamber & Oral Chamber
Via Proboscis Tubes & Open
Duck Valves

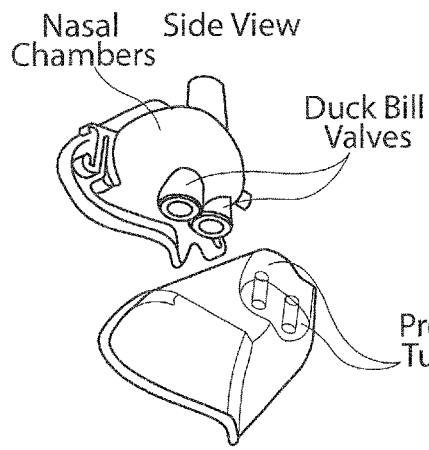
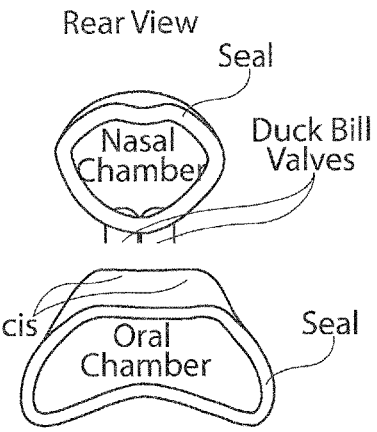
Figure 18A
Figure 18B
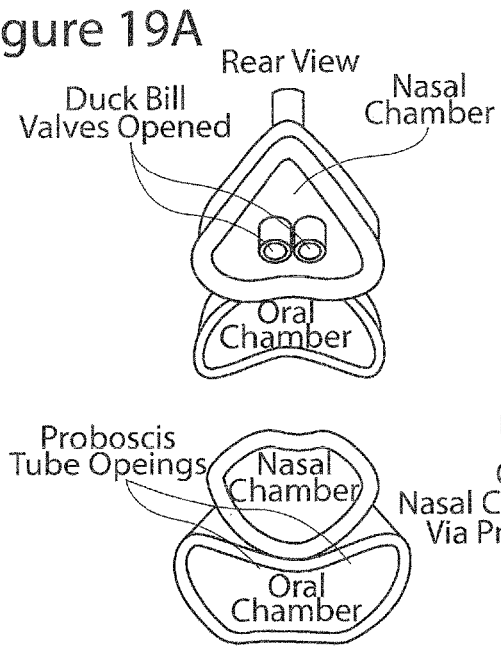
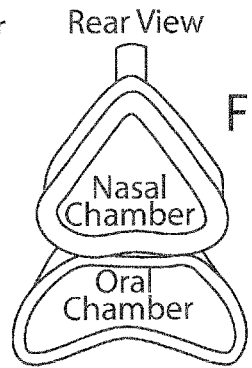
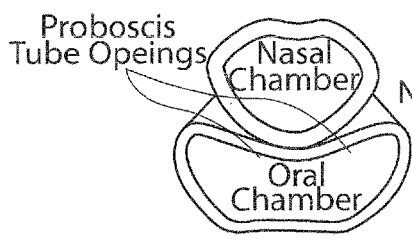
Figure 19A
Figure 19B
Figure 19C

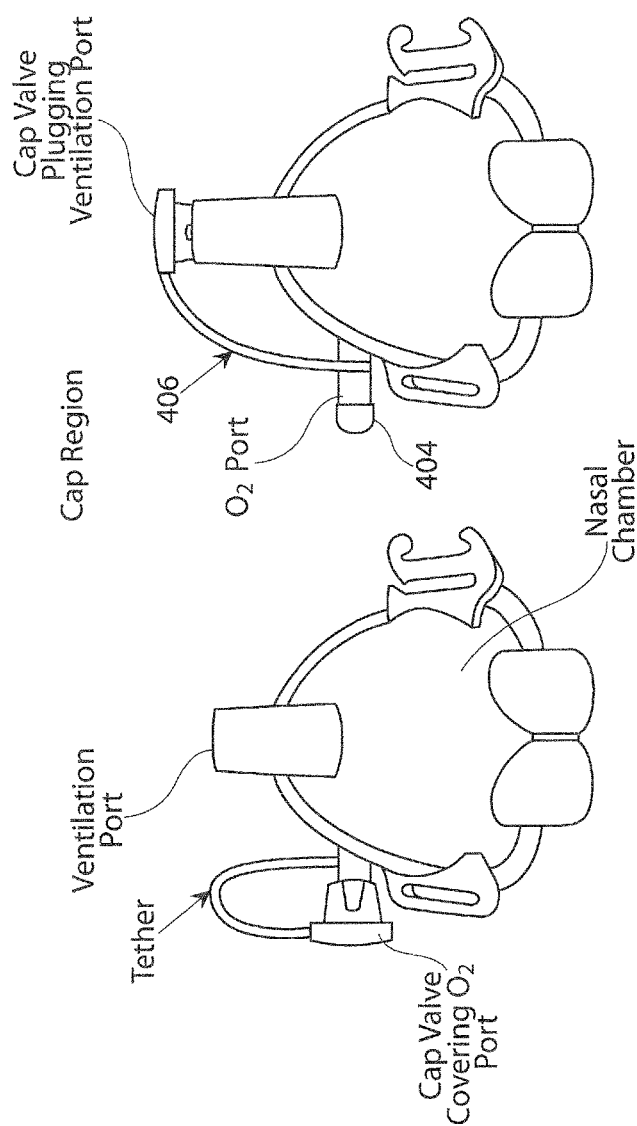

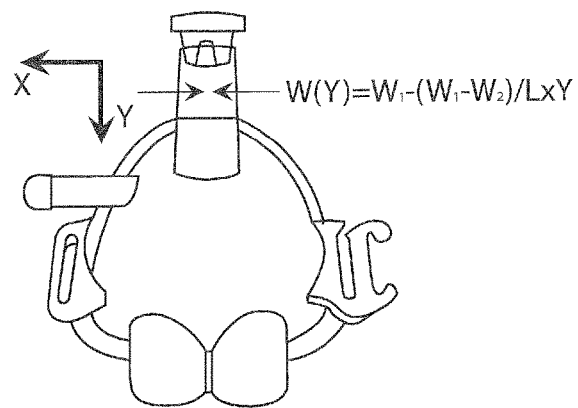
Cap Valve, Ventilation Port
Partially Open
Figure 20C
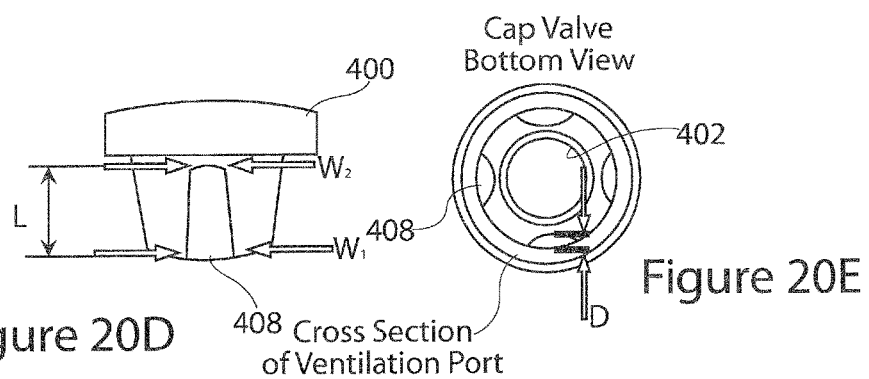
Figure 20D
Figure 20E Mask Anchor head strap Mask Anchor head strap attaching
to both clips & Mask Anchor clips The distal end of the centered Mask Anchor
Arm extension maintaining head/neck positioning
while head/neck angles are changed Mask Anchor ring with spike cleats Mask Anchor ring with spike cleats around a mask

Sniff Position

Vertical Position

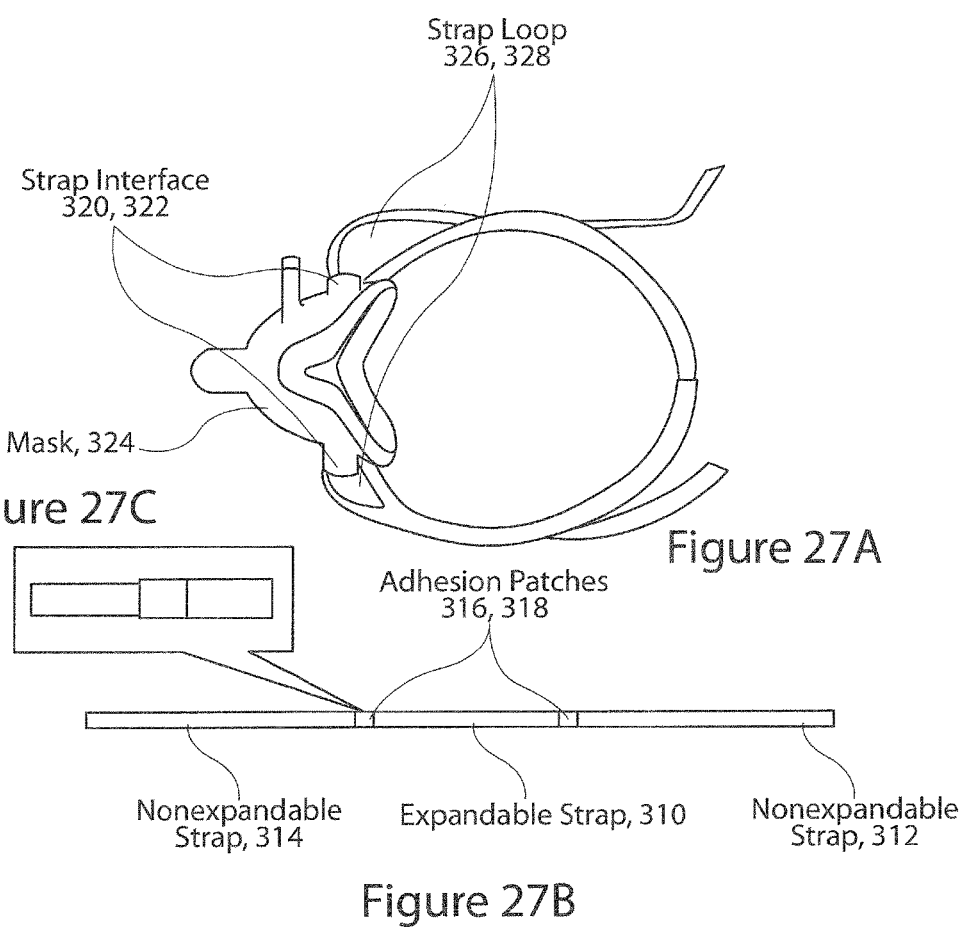

COMBINED NASAL AND MOUTH VENTILATION MASK

CROSS REFERENCE TO RELATED APPLICATIONS

This application is a continuation of U.S. application Ser. No. 15/127,760, filed Sep. 20, 2016, which is turn claims priority from PCT Patent Application Serial No. PCT/US15/34277 filed Jun. 4, 2015, which claims priority from U.S. Provisional Application Ser. No. 62/007,802, filed Jun. 4, 2014, and from U.S. Provisional Application Ser. No. 62/056,293, filed Sep. 26, 2014, and from U.S. Provisional Application Ser. No. 62/060,417, filed Oct. 6, 2014, and from U.S. Provisional Application Ser. No. 62/061,045, filed Oct. 7, 2014, and from U.S. Provisional Application Ser. No. 62/065,504, filed Oct. 17, 2014, and from U.S. Provisional Application Ser. No. 62/091,370, filed Dec. 12, 2014, and from U.S. Provisional Application Ser. No. 62/118,301, filed Feb. 19, 2015, and from U.S. Provisional Application Ser. No. 62/149,313, filed Apr. 17, 2015, and from U.S. Provisional Application Ser. No. 62/161,086, filed May 13, 2015, and from U.S. Provisional Application Ser. No. 62/161,093, filed May 13, 2015, the contents of which are incorporated herein by reference.

BACKGROUND OF THE INVENTION

During surgery a patient usually is placed under anesthesia and the most common delivery system consists of canisters containing anesthesia gases and oxygen, a system of regulating gas flow and the patient's breathing, and a device ensuring the potency of the patient's airway for breathing, oxygenation and the delivery of an anesthetic gas mixture. A mask is used to provide oxygen to the patient either before the patient is anesthetized, while the patient is anesthetized, or if the patient is sedated during the surgery or procedure. However, one of the drawbacks of mask ventilation is that it requires constant contact between the provider's hands and the patient's face to hold the mask in place and keep the patient in the sniffing position in order to ensure that oxygen and anesthetic gases do not leak out into the air and that the patient's airway remains patent. If the provider does not maintain the patient in the sniffing position, a dangerous complication known as upper airway obstruction may occur. The reason the provider needs to perform continuous mask holding and maneuvering is due to the human anatomy and physiology. When muscles of the jaw, tongue and upper airway relax due to sedatives and/or muscle relaxants given to the patient for sedation and/or anesthesia, wherein, the jaw of the patient drops and the tongue obstructs the airway resulting in snoring (partial obstruction) or apnea (complete inability for oxygen to pass via the upper airway into the lungs), the upper airway (mouth, pharynx, larynx) may become partially obstructed and possibly completely closed. Another problem exists when a provider fails to administer enough anesthesia or sedative or the anesthesia or sedative begins to wear off and the patient begins to move. This can cause the patient's airway to obstruct as well since the patient's head and neck position are no longer in the sniffing position. Patient movement during surgery also can be dangerous because it can cause the surgeon to make a mistake, particularly in eye, ear, nose, neck, head, and throat surgery.

Notwithstanding the aforesaid potential problems, the use of facemasks, whether nasal masks, which only cover the nose, or facemasks, which cover both the nose and mouth, to apply inhalational agents, such as oxygen or volatile anesthetic gases, is essentially universal in the medical field. However, up until now, nasal masks and facemasks have been used separately as either nasal masks alone or facemasks alone. A significant clinical need has emerged, where combining a nasal mask with a mouth mask into one could have a substantial impact on patient safety during both endotracheal intubation and monitored anesthesia care cases involving sedation. For example, current standard of care recommends pre-oxygenating (delivering 100% oxygen via facemask) a patient for several minutes prior to endotracheal intubation in order to fill the patient's lungs with oxygen. Also, pre-oxygenating a patient significantly lengthens the time (2-8 minutes) that patient begins to desaturate (blood-oxygen levels begin to fall to critically low levels). Exemplary of gas inhalation masks used in administering general anesthesia (GA) to a patient is that disclosed in U.S. Pat. No. 5,975,079 (Hellings et al). As indicated by this patent, an acceptable anesthesia mask should be disposable, made of transparent material, have a strap or straps to hold the mask in place, when desired, be of sufficient size to cover the patient's nose and mouth, and have a pneumatic sealing cushion, not only to promote patient comfort, but to prevent exposing the medical staff to anesthesia or other applied gas or gases. See also U.S. Pat. No. 8,336,549 B2 in which there is discussed a disposable anesthesia face mask comprising a shell member having an annular flange and a donut shaped pneumatic sealing cushion attached to the shell member annular flange. The shell member and its flange are "pear-shaped" defining a nasal portion of first transverse extent, a mouth portion of second transverse extent, and an under-the-chin engagement portion of third transverse extent, where the second transverse extent is greater than the first transverse extent and the third transverse extent is greater than the second transverse extent.

Other prior art anesthesia masks and CPAP masks are described in U.S. Pat. No. 5,738,094; US 2014/0083425; US 2003/0024533; U.S. Pat. No. 6,779,524; US 2014/0076311; U.S. Pat. Nos. 8,001,968, 6,112,746; 8,528,558; 7,178,524; 7,036,508; 5,560,354; US 2015/0059759; and U.S. Pat. No. 5,243,971

Furthermore, mask straps and harnesses are commonly used to hold masks on a patient. However, a common problem in the majority of cases today with the use of currently available mask straps and/or the head harness is that they still require the provider to hold and maneuver the mask continuously during the surgery because there is no way of fixing patient's head and neck to a surface. U.S. Pat. No. 6,981,503 B1 (hands-free anesthesia mask) proposes a way of attaching a head strap to the face; however, it does not provide a means of restricting head and neck movement. Many times when the patient is relaxed with sedation and anesthesia the head falls forward, causing collapse of the airway. One way to solve this problem is to fix the patients face mask or head to a base surface which will prevent it from falling forward. Also, to avoid partial and/or complete obstruction the provider can perform a maneuver called the "jaw thrust" maneuver. The "jaw thrust" maneuver" is done with one hand moving the jaw up and forward to move the tongue so that the airway is opened. The "jaw thrust" is performed while holding a mask over the patient's mouth and nose to deliver oxygen. In order to ventilate the patient while performing a "jaw thrust" the provider is required to hold the mask over the patient's face almost constantly and prevents the ability to perform other tasks during the surgery. This has led to a significant loss of popularity of the mask anesthetics and the increased use of other airway devices, which are more invasive and have greater potential side effects and complications. Also, a problem exists that when a mask is adjusted on a patient when in a sniff position, when the patient's head is moved to a more natural or "vertical" position, e.g., post operation, the mask becomes loose on the patient's head. See also U.S. Pat. Nos. 6,439,231; 6,003,511; 5,983,896; 5,778,872; 4,265,235; 5,404,873; 3,856,051; 3,556,097; 4,007,737; 4,188,946; 4,265,235; 4,463,755; 4,232,667; 4,596,246; 5,121,746; 5,284,160; 5,778,872; and U.S. Pat. No. 6,129,082; U.S. 2003/0183232 A1; U.S. Pat. Nos. 3,815,596; 5,462,050; 6,035,852; 6,412,488; 6,736,139; 6,792,943; 6,981,503; 7,753,051 6,981,503 B1; 7,753,051; U.S. 2009/0178680; U.S. Pat. Nos. 4,905,712; 3,889,668; 3,897,777; US 2007/0295335.

In our co-pending PCT Application Serial No. PCT/US14/44934, we provide an improved mask strap system for an anesthesia mask that allows hands-free patient ventilation while maintaining the patient in the sniffing position and preventing head and neck movement. We also provide an anesthesia strap system for maintaining an anesthesia face mask on the head of the user, that prevents movement of the patient's head and neck, and can be placed in front of the patient's face. Therefore if the patient is already lying down, sedated, or anesthetized, the provider will not have to lift the patient's head off the table. We also provide an anesthesia mask anchor ring system including a plurality of elastomeric cords connecting the mask anchoring to a support.

SUMMARY OF THE INVENTION

The present invention provides improvements over the foregoing and other prior art, and helps to solve the problem of patient's desaturating by maintaining ventilation even during intubation. The present invention in one aspect provides a gas ventilation mask comprising an anesthesia nasal mask and a mouth or oral mask defining respectively a nasal chamber and an oral chamber, detachably connected to one another so that the nasal mask may be used either separately as a nasal mask, or together with the mouth mask as a combination nasal-mouth mask.

In another aspect of the invention, the mask is characterized by one or more of the following features:

(a) wherein the nasal and oral chambers are connected to one another through a self-closing valve or passage, preferably a septum or duck valve or passage;

(b) further including at least one ventilation or oxygen port communicating with the nasal chamber, wherein at least one of the ventilation or oxygen port preferably is offset to a side of the nasal chamber;

(c) comprising both a ventilation port and an oxygen port communicating with the nasal chamber, wherein at least one of the ventilation port and/or the oxygen port preferably is offset to a side of the nasal chamber, and further comprising a removable stopper or cap for at least one of the ports;

(d) wherein the mask is formed at least in part of a transparent material to permit visualization of condensation or aspiration;

(e) further comprising a multi-lobed, preferably Y-shaped seal that interfaces with the patient's face and the oral and/or nasal ventilation chambers of the mask;

(f) further comprising a J-shaped seal, connected to the oral chamber that seals the oral chamber and nasal chamber interface when the two chambers are engaged, preventing gas from escaping through that interface;

(g) further comprising a multi-lobed, preferably Y-shaped seal on the nasal chamber that over-laps the J-shaped seal of the oral chamber, preventing gas from escaping that interface when both chambers are pressured;

(h) further comprising a mask strap anchor pair that has one closed side for accommodating a strap attached and an open side, or two open sides, wherein the open side or sides allows a care provider to attach the strap to a patient, wherein the open side or sides preferable are oriented up so that when strap tension force is applied, the force is resisted by a bottom portion of the strap anchor in order that the strap does not slide off the anchor; and (i) further comprising grip indents on the left and right surfaces of the oral chamber for gripping by a care provider in placing the mask onto a patient's face.

In another aspect of the invention, the mask comprises a nasal cushion including a nasal bridge region, a check region, and an upper lip region, and a mouth cushion including a lower lip region, a cheek region, and an upper lip region; a first nasal membrane or seal comprising a substantially triangularly shaped frame of resiliently deformable material having a first molded inwardly curved rim of the first nasal membrane or seal; a second nasal membrane or seal of resiliently deformable material, the second nasal membrane or seal being thinner, as thin, or thicker than the first nasal membrane or seal, the second nasal membrane or seal having a second molded inwardly curved rim, the second nasal membrane or seal curved rim spaced a first distance from the first nasal membrane or seal curved rim in the cheek region and the second nasal membrane or seal curved rim spaced a second distance from the first nasal membrane or seal curved rim in the nasal bridge region, the second distance being greater than the first distance. The first and second distances being measured when the mask is not in use. A portion of the second membrane or seal curved rim forms a face contacting seal. A first mouth membrane or seal comprises a substantially oval shaped frame of resiliently deformable material having a first molded inwardly curved rim of the first mouth membrane or seal; a second mouth membrane or seal of resiliently deformable material, being thinner, as thin, or thicker than the first mouth membrane or seal, has a second molded inwardly curved rim. The second mouth membrane or seal curved rim is spaced a third distance from the first mouth membrane or seal curved rim in the cheek region and the second mouth membrane or seal curved rim is spaced a fourth distance from the first mouth membrane or seal curved rim in the mouth region. The fourth distance is greater than the third distance, the third and fourth distances being measured when the mask is not in use, a portion of the second membrane or seal curved rim forming a face contacting seal.

In still yet another aspect of the invention, the mask as above described is characterized by one or more of the following features:

(a) wherein the second molded rim and the first molded rim have a co-located notch to accommodate the bridge of a wearer's nose; wherein the first nasal membrane or seal molded rim and the second nasal membrane or seal molded rim preferably are substantially saddle-shaped, wherein the second nasal membrane or seal preferably is shaped so that the seal portion, in use, contacts at least the wearer's nose; and, wherein the seal portion, in use, preferably contacts the wearer's facial tissue around the sides and over the bridge of the wearer's nose, and between the base of the wearer's nose and the top wearer's lip;

(b) wherein the second rim and seal portion are shaped to generally match facial contours of the wearer in the region of facial tissue around the sides and over the bridge of the wearer's nose, and between the base of the wearer's nose and the wearer's upper lip;

(c) wherein the first and second nasal membranes or seals comprise single molded pieces;

(d) wherein the first molded inwardly curved rim of the first nasal membrane or seal is as thick, less thick, or thicker than the second nasal membrane or seal; and (e) wherein the second molded inwardly curved rim of the second nasal membrane or seal is as thick, less thick, or thicker than the first nasal membrane or seal.

In a still further aspect of the invention the mask includes a mask body for connection with a supply of breathable gas; and a nasal cushion secured to the mask body, the mask body and the cushion forming a nose-receiving cavity. The cushion includes: a nasal bridge region, a cheek region and an upper lip region; and a substantially triangularly-shaped first nasal membrane or seal of resiliently deformable material is provided having a first molded inwardly curved rim to surround wearer's nose. A second nasal membrane or seal also formed of resiliently deformable material is provided. The second membrane or seal is relatively more flexible than the first nasal membrane or seal. The second nasal membrane or seal has a second molded inwardly curved rim, the second molded rim being of the same general shape as the first molded rim and being fixed to and extending away from the first nasal membrane or seal so as to have a second nasal membrane or seal inner surface spaced a first distance from an outer surface of the first molded rim in the wearer's cheek region. The second membrane or seal inner surface is spaced a second distance from the first nasal membrane or seal outer surface of the first molded rim in the nasal bridge region. The second distance is greater than the first distance, when the first and second distances are measured when the mask is not in use. A portion of the second molded rim forms a face contacting seal, wherein the portion preferably is substantially coterminous with respect to said second molded rim and is resiliently deformable towards said first nasal membrane or seal.

In another aspect of the invention, the mask is characterized by one or more of the following features:

(a) the second membrane or seal molded rim and the first nasal membrane or seal molded rim preferably each have a co-located notch to accommodate the bridge of a wearer's nose. The first and second molded rims preferably are substantially saddle-shaped. The second nasal membrane or seal preferably is shaped so that the seal portion, in use, contacts at least the wearer's nose. And, wherein the seal portion, in use, contacts the wearer's facial tissue around the sides and over the bridge of the wearer's nose, and between the base of the wearer's nose and the wearer's upper lip of the wearer; and (b) wherein the rim and the seal portion are shaped to generally match facial contours in the region of facial tissue around the sides and over the bridge of the wearer's nose, and between the base of the nose and the upper lip of the wearer.

The present invention also provides a nasal CPAP treatment apparatus and a oral/nasal full face mask comprising: a generator, ventilator or $O_2$ source for the supply of gas at a pressure elevated above atmospheric pressure; a gas delivery conduit coupled to the generator; and a nasal mask or a full face mask that comprises a nasal cushion including a nasal bridge region, a cheek region, and an upper lip region, and a mouth cushion including a lower lip region, a cheek region, and an upper lip region; a first nasal membrane or seal comprising a substantially triangularly shaped frame of resilient material having a first molded inwardly curved rim of the first nasal membrane or seal; a second nasal membrane or seal of resilient material, said second nasal membrane or seal being thinner, as thin, or thicker than the first nasal membrane or seal. The second nasal membrane or seal has a second molded inwardly curved rim, the second nasal membrane or seal curved rim being spaced a first distance from the first nasal membrane or seal curved rim in the cheek region and the second nasal membrane or seal curved rim being spaced a second distance from the first nasal membrane or seal curved rim in the nasal bridge region. The second distance is greater than the first distance, the first and second distances being measured when the mask is not in use. A portion of the second membrane or seal curved rim forms a face contacting seal. A first mouth membrane or seal comprises a substantially oval shaped frame of resiliently deformable material having a first molded inwardly curved rim of the first mouth membrane or seal; a second mouth membrane or seal of resilient material, the second mouth membrane or seal being thinner, as thin, or thicker than the first mouth membrane or seal, the second mouth membrane or seal having a second molded inwardly curved rim. The second mouth membrane or seal curved rim is spaced a third distance from the first mouth membrane or seal curved rim in the cheek region and the second mouth membrane or seal curved rim being spaced a fourth distance from the first mouth membrane or seal curved rim in the mouth region. The fourth distance is greater than the third distance, the third and fourth distances being measured when the mask is not in use, a portion of the second membrane or seal curved rim forming a face contacting seal.

In another aspect of the invention, the CPAP as above described is characterized by one or more of the following features:

(a) wherein the first and second molded rims preferably each have a co-located notch to accommodate the bridge of a wearer's nose. The first and second molded rims preferably are substantially saddle-shaped. The second nasal membrane or seal preferably is shaped so that the seal portion, in use, contacts at least the wearer's nose. The seal portion, in use, contacts the facial tissue around the sides and over the bridge of the nose, and facial tissue around the sides and over the bridge of the nose, between the base of the nose and the upper lip and between the base of the nose and the upper lip of the wearer;

(b) wherein the second molded rim and the seal portion are shaped to generally match facial contours in the region of facial tissue around the sides and over the bridge of the wearer's nose, between the base of the wearer's nose and the wearer's upper lip and between the base of the wearer's nose and the wearer's upper lip of the wearer. The second molded rim and the first molded rim preferably have a co-locating rim to accommodate the lips of a wearer's mouth. The first mouth membrane or seal molded rim and the second mouth membrane or seal molded rim preferably are substantially oval shaped. The second mouth membrane or seal preferably is shaped so that the seal portion, in use, contacts at least a wearer's upper and lower lip, and also preferably contacts the facial tissue around the sides and over the upper and lower lips of the mouth of the wearer. The second rim and seal portion preferably are shaped to generally match facial contours in the region of facial tissue around the sides and over the upper and lower lip of the mouth of the wearer. The first and second mouth membranes or seals preferably comprise one molded pieces, wherein the first molded inwardly curved rim of the first mouth membrane or seal preferably is as thick, less thick, or thicker than the second mouth membrane or seal, and wherein the second molded inwardly curved rim of the second mouth membrane or seal preferably is as thick, less thick, or thicker than the first mouth membrane or seal.

The present invention also provides a mask for connection to a wearer's face comprising: a mask body for connection to a supply of breathable gas; and a mouth cushion secured to said mask body. The mask body and cushion form a mouth-receiving cavity. The cushion includes: a mouth region, a cheek region and an upper and lower lip region. A substantially oval-shaped first mouth membrane or seal of resilient material has a first molded inwardly curved rim to surround the wearer's mouth; a second mouth membrane or seal also formed of resiliently deformable material, the second mouth membrane or seal being relatively more flexible than the first mouth membrane or seal. The second mouth membrane or seal has a second molded inwardly curved rim, the second molded rim being of the same general shape as the first molded rim and fixed to and extending away from the first mouth membrane or seal so as to have a second mouth membrane or seal inner surface spaced a first distance from an outer surface of the first molded rim in the cheek region. The second mouth membrane or seal inner surface is spaced a second distance from the first mouth membrane or seal outer surface of the first molded rim in the mouth region. A portion of the second molded rim forms a face contacting seal. The seal portion is substantially coterminous with respect to the second molded rim and is resiliently deformable towards the first mouth membrane or seal in use of the mask.

In another aspect of the invention, the aforesaid mask is characterized by one or more of the following features:

(a) the second membrane or seal molded rim and the first mouth membrane or seal molded rim preferably each have a co-located rim to accommodate the wearer's mouth. The first and second molded rims preferably are substantially oval-shaped. The second mouth membrane or seal preferably is shaped so that the seal portion, in use, contacts at least the wearer's mouth. The seal portion, in use, preferably contacts the facial tissue around the sides and over the wearer's mouth, and between the wearer's upper and wearer's lower lip, wherein said rim and said seal portion preferably are shaped to generally match facial contours in the region of facial tissue around the sides and the wearer's mouth, and between the wearer's upper and wearer's lower lip.

(b)(1) Optionally, the mask has a ventilator circuit port, projecting from a side of the nasal chamber as a straight port nominally located in an X-Y plane located on a left side of the patient projecting in a negative X direction or essentially parallel to the X axis, wherein the angle of the port relative to the X axis preferably projects at an angle that varies from plus 90 degrees to negative 90 degrees.

(b)(2) Optionally, the mask has a ventilator circuit port projecting from a side of the nasal chamber as a straight port nominally located in an X-Y plane located on the right side of the patient projecting in the positive X direction or essentially parallel to the X axis, wherein the angle of the port relative to the X axis preferably projects at an angle that varies from plus 90 degrees to negative 90 degrees.

(b)(3) Optionally, the mask has a straight ventilator circuit port that is at an angle nominally located in the X-Y plane, wherein the ventilator circuit port preferably projects to an angle out of that plan by plus 90 degrees to negative 90 degrees.

(b)(4) Optionally, the mask has an alternate ventilator circuit port, projecting from a top of the nasal chamber in the negative Y direction as an elbowed port nominally located in the X-Y plane, wherein an open end of the elbow that connects with the ventilator points to a right side of the patient projecting in a positive X direction or essentially parallel to the X axis, wherein the angle of the elbowed port relative to the X axis preferably projects at an angle that varies from plus 90 degrees to negative 90 degrees.

(b)(5) Optionally, the mask has an alternate ventilator circuit port, projecting from a top of the nasal chamber in the negative Y direction as an elbowed port nominally located in the X-Y plane, wherein an open end of the elbow that connects with the ventilator points to a left side of the patient projecting in a negative X direction or essentially parallel to the X axis, wherein the angle of the elbowed port relative to the X axis preferably projects at an angle that varies from plus 90 degrees to negative 90 degrees, wherein the angle of the elbow portion of the alternate ventilator circuit port, preferably also projects at an angle out of the plane by plus 90 degrees to negative 90 degrees.

(b)(6) Optionally, the mask has an oxygen port projecting from a side of the nasal chamber as a straight port nominally located in an X-Y plane located on a left side of the patient projecting in the negative X direction that can be parallel to the X axis, wherein the angle of the port relative to the X axis preferably projects at an angle that varies from plus 90 degrees to negative 90 degrees.

(b)(7) Optionally, the mask has an oxygen port projecting from the side of the nasal chamber as a straight port nominally located in an X-Y plane located on a right side of the patient projecting in the positive X direction that can be parallel to the X axis, wherein the angle of the port relative to the X axis preferably projects at an angle that varies from plus 90 degrees to negative 90 degrees.

(b)(8) Optionally, the mask has an oxygen port, projecting from a top of the nasal chamber in a negative Y direction as an elbowed port nominally located in an X-Y plane, wherein the open end of the elbow that connects with the ventilator points to a right side of the patient projecting in the positive X direction that can be parallel to the X axis, wherein the angle of the elbowed port relative to the X axis preferably projects at an angle that varies from plus 90 degrees to negative 90 degrees.

(b)(9) Optionally, the mask has an oxygen port projecting from a top of the nasal chamber in a negative Y direction as an elbowed port nominally located in an X-Y plane, wherein the open end of the elbow that connects with the ventilator points to a left side of the patient projecting in the negative X direction that can be parallel to the X axis, wherein the angle of the elbowed port relative to the X axis preferably projects at an angle that varies from plus 90 degrees to negative 90 degrees.

(b)(10) Optionally, the mask has an alternate ventilator circuit port projecting from a front of the nasal chamber in the positive Z direction as an elbowed port, wherein an open end of the elbow that connects with the ventilator is pointing to a left side of the patient projecting in a negative X direction or essentially parallel to the X axis, nominally in the X-Y plane, wherein the angle of the elbowed port relative to the X axis preferably projects at an angle that varies from plus 180 degrees to negative 180 degrees, or wherein the angle of the elbow portion of the alternate ventilator circuit port, that is nominally located in the X-Y plane also preferably projects at an angle out of that plane by plus 90 degrees to negative 90 degrees.

(b)(11) Optionally, the mask has an oxygen port, projecting from a front of the nasal chamber in a positive Z direction as an elbowed port, wherein an open end of the elbow that connects with the ventilator points to s left side of the patient projecting in a negative X direction or essentially parallel to the X axis, nominally in the X-Y plane, wherein the angle of the elbowed port relative to the X axis preferably projects at an angle that varies from plus 180 degrees to negative 180 degrees, or wherein the angle of the oxygen port elbow portion that is nominally located in the X-Y plane preferably also projects to an angle out of that plane by plus 90 degrees to negative 90 degrees.

(b)(12) Optionally, the mask has a ventilator circuit port projecting from a side of the Nasal Chamber as a straight port nominally located in a Y plane located in a center side of the patient projecting in the negative y direction.

(b)(13) Optionally, the mask has an oxygen port projecting from a side of the nasal chamber as a straight port nominally located in a X-Y plane located on a left side of the patient projecting in the negative X direction or essentially parallel to the X axis, wherein the angle of the port relative to the X axis projects at an angle that varies from plus 90 degrees to negative 90 degrees.

(b)(14) Optionally, the mask has an alternate ventilator circuit port projecting from a front of the nasal chamber in a positive Z direction as an elbowed port, wherein the elbow has an ability to swivel 360 degrees about the Z axis of the straight port connected to the nasal chamber, wherein the swivel elbow preferably is nominally a 90 degree elbow.

(b)(15) Optionally, the mask has a straight ventilator port connected to the nasal chamber in any location.

(b)(16) Optionally, wherein the nasal chamber of the mask is configured with one or more ventilator circuit ports and zero or one or more oxygen ports.

(b)(17) Optionally, wherein nasal chamber of the mask is designed to operate under a positive gauge pressure relative to the ambient atmosphere at a pressure less than or equal to 90 cm of water.

(b)(18) Optionally, wherein the nasal and oral chambers of the mask, when connected, are designed to operate under a positive gauge pressure relative to the ambient atmosphere at a pressure less than or equal to 90 cm of water.

(b)(19) Optionally, the nasal chamber is designed to operate under a negative gauge pressure relative to the ambient atmosphere at a pressure greater than or equal to negative 10 pounds of force per square inch.

(b)(20) Optionally, the nasal and oral chambers, when connected, are designed to operate under a negative gauge pressure relative to the ambient atmosphere at a pressure greater than or equal to 10 pounds of force per square inch.

In yet another embodiment of the invention there is provided a nasal mask comprising a ventilation port, an $O_2$ port and a cap or plug interchangeable between the ventilation port and the $O_2$ port.

The present invention in yet another aspect provides improvements in devices for holding a mask in position on a patient, and in another aspect for holding a patient's head in position. More particularly, in one aspect of the invention, there is provided a mask anchor for holding a face mask on a patient, comprising a head bonnet for engaging a back of a patient's head, a posterior head strap that originates from behind the patient's head, in contact with the patient's head and attaches either directly or indirectly to the mask when the mask is on the patient's face, wherein the strap can be tightened to create a seal to allow for positive pressure ventilation or left loose and for providing supplement oxygen.

In another embodiment the mask anchor may include one or more straps for attachment to a base/surface, for securing the mask to the patient's face and also for securing the patient's head to the base/surface and for stabilizing the patient's head in position.

In another embodiment, the mask anchor comprises three straps, a first side strap, a second side strap and a third side strap approximately evenly spaced from and joined to the first strap and the second strap, and positioned posteriorly.

In one embodiment the posterior head strap is attached directly to the mask, or the first and second straps are attached directly to the mask.

In yet another embodiment, the posterior head strap is attached to an anchor ring which in turn is placed on the mask, or the first and second side straps attach to a mask anchor ring which is placed over the mask.

The present invention also provides a mask strap system including an expandable strap portion, having the ability to extend up to twice its length or more when the patient is in a sniff position, so as to maintain tension on the mask when the patient is placed in a natural or "vertical" position.

In one embodiment the anesthesia mask strap system comprises an expandable strap portion having the ability to extend; second and third non-expandable strap sections fixed to ends of the expandable strap section; and an adhesion section or device for fixing a length of the strap system when the second and third non-expandable strap sections are pulled to tension the expandable strap section. Preferably, the expandable strap section has the ability to extend up to twice its length, or more, and is formed of a resiliently expandable elastic material.

In yet another aspect of the mask strap system, the second and third non-expandable strap sections are fixed by adhesion to themselves. In such aspect the adhesion comprises hook and loop fasteners, or a mechanical clasp, such as a gripper, a suspender-type no-slip clasp, a button and buttonhole, or a tab and belt hole.

In another and preferred aspect of the mask strap system, the strap system length is fixed by folding the second and third non-expandable strap sections back on themselves.

In still yet another embodiment of the mask strap system, the second and third non-expandable strap sections are fixed to a patient head support or a table supporting the patient.

The present invention also provides an anesthesia mask having a strap system as above described.

The present invention also provides an anesthesia mask comprising an anesthesia nasal mask and a mouth mask defining respectively a nasal chamber and an oral chamber, detachably connected to one another so that the nasal mask may be used either separately as a nasal mask, or the nasal mask and the mouth mask used together as a combination nasal-mouth mask. The anesthesia mask preferably has two sets of retention straps, each comprising a first expandable strap portion having the ability to extend and second and third non-expandable portions fixed to ends of the first expandable strap portions, respectively and an adhesive section or device for fixing a length of the strap system when the second and third non-expandable strap sections are pulled to tension the expandable strap section, attached respectively to the nasal chamber and the oral chamber. In a preferred embodiment, the adhesion section comprises hook and loop fasteners.

With the current invention, the combined nasal mask and oral mask, can be used together as a facemask to ventilate a patient either prior to endotracheal intubation or during general anesthesia (GA), or the mouth mask can be separated from the nasal mask and the nasal mask used to apply continuous positive airway pressure (CPAP) to help maintain a patent airway and ventilate a patient while the anesthesiologist attempts intubation, which will significantly prolong the time until the patient begins to desaturate. The current invention also is useful during sedation cases, especially for deep sedation or for patients with Obstructed Sleep Apnea (OSA) or obesity, where the upper airway of many of these patients becomes obstructed and prevents or impedes breathing. The mouth mask of the current invention also can be separated from the nasal mask and the nasal mask can be used to apply continuous positive airway pressure (CPAP) to help relieve the upper airway obstruction, maintain a patent airway, and assist in ventilation during the case. The combined nasal and mouth mask of the current invention also is useful in situations where a nasal mask is not sufficient to ventilate the patient. With the mask of the present invention one can reattach the mouth mask and the mask used for traditional bag-mask ventilation. The mask of the present invention also permits a health care provider to apply nasal CPAP during semi-awake fiberoptic intubations, where being able to maintain a patient's oxygen saturation levels may be critical, or to apply PEEP to mechanically ventilated patients. Yet another feature and advantage of the mask of the present invention over the prior anesthesia mask art is the ability to secure not only the combined nasal mask and mouth mask to the patient's face allowing for hands-free ventilation, but also to secure the patient's head and neck in place by attaching to a surface and maintaining the patient in a position that ensures a patent airway, which is critical for oxygenation and ventilation.

BRIEF DESCRIPTION OF THE DRAWINGS

Further features and advantages of the present invention will be seen from the following detailed description, taken in conjunction with the accompanying drawings, wherein like numerals depict like parts, and wherein:

FIG. 1 is a front view of a combined nasal mask and oral mask in accordance with the present invention;

FIG. 2A is a rear view of the mask of FIG. 1;

FIG. 3 is an exploded view of the mask of FIG. 1;

FIG. 9A is an interior view of a combined nasal mask and oral mask in accordance with the present invention;

FIG. 9B is a side elevational view of a combined nasal mask and oral mask in accordance with the present invention;

FIG. 9C is a plan view of combined nasal mask and oral mask in accordance with the present invention;

FIGS. 9D and 9E are enlarged views of a J-shaped seal element of the combined nasal mask and oral mask in accordance with the present invention;

FIG. 9F is an enlarged view of a "Y" seal of a combined nasal mask and oral mask in accordance with the present invention;

FIG. 10 is a side elevational view showing a combined nasal mask and oral mask on a patient in accordance with the present invention;

FIGS. 12A-12D show the J-shaped seal element in accordance with the present invention;

FIGS. 13A-19C are views of an alternative and preferred embodiment of combined nasal mask and oral mask in accordance with the present invention;

FIGS. 20A-C illustrate use of the nasal chamber portion of the mask for continuous positive airway pressure, and FIGS. 20D and 20E are side and end views of a cap valve useful with the nasal chamber portion of the mask of FIGS. 20A and 20B;

FIG. 27A is a top plan view of a ventilation mask with a strap system in accordance with the present invention;

FIG. 27B is a side elevational view of the strap system;

FIG. 27C is an enlarged view of a portion of the strap illustrated in FIG. 27B;

DETAILED DESCRIPTION OF THE INVENTION

As used herein, unless otherwise stated, the mask of the present invention advantageously may be used for delivering anesthesia, for positive pressure ventilation, CPAP, administration of supplemental oxygen, or PEEP (positive and expiratory pressure) in connection with a variety of pressurized gas sources including ventilation circuits, AMBU bags, oxygen canisters, etc.

Also, as used herein, the term "nasal mask" and "nasal chamber", and "oral mask" and "oral chamber", respectively, may be used interchangeably.

Figures 2B, 2C:
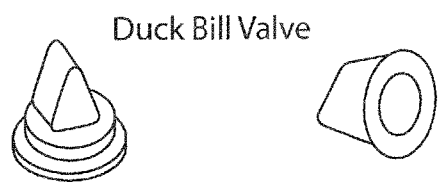
FIGS. 2B-2D show details of the duck valve portion of the nasal mask chamber of FIG. 1.
Figure 2D:
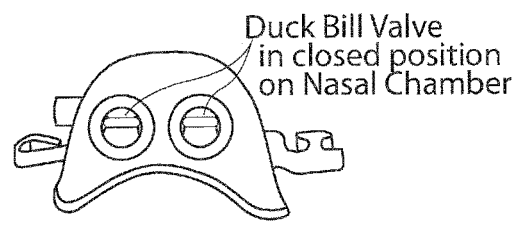
Figure 2E:
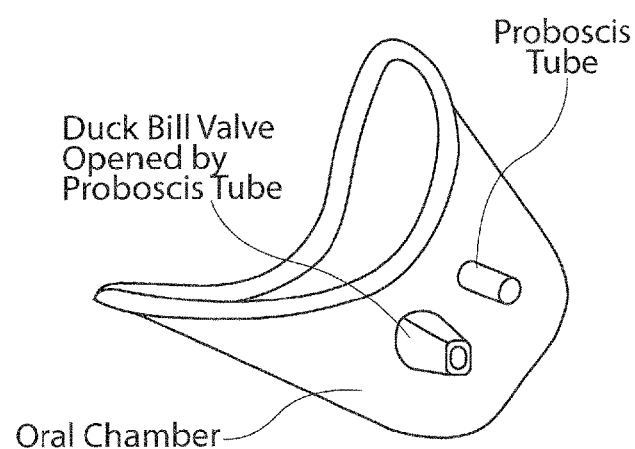
FIG. 2E shows details of the oral mask chamber of FIG. 1.
Figure 4:
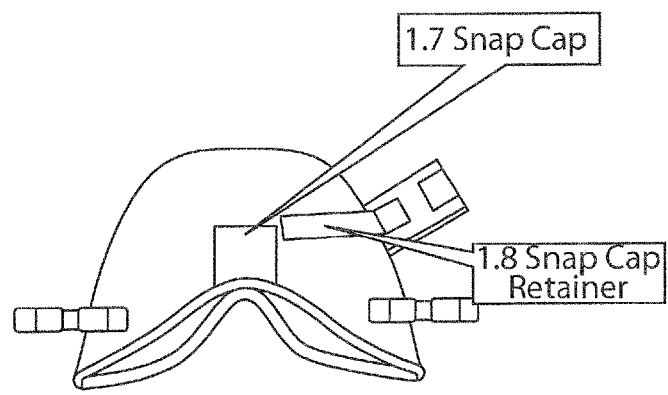
FIG. 4 is a bottom view of the nasal chamber portion of the mask of FIG. 1.
Figure 4A:
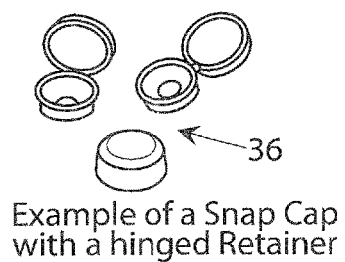
FIG. 4A is a perspective view of snap caps for use with the mask.
Figure 5:
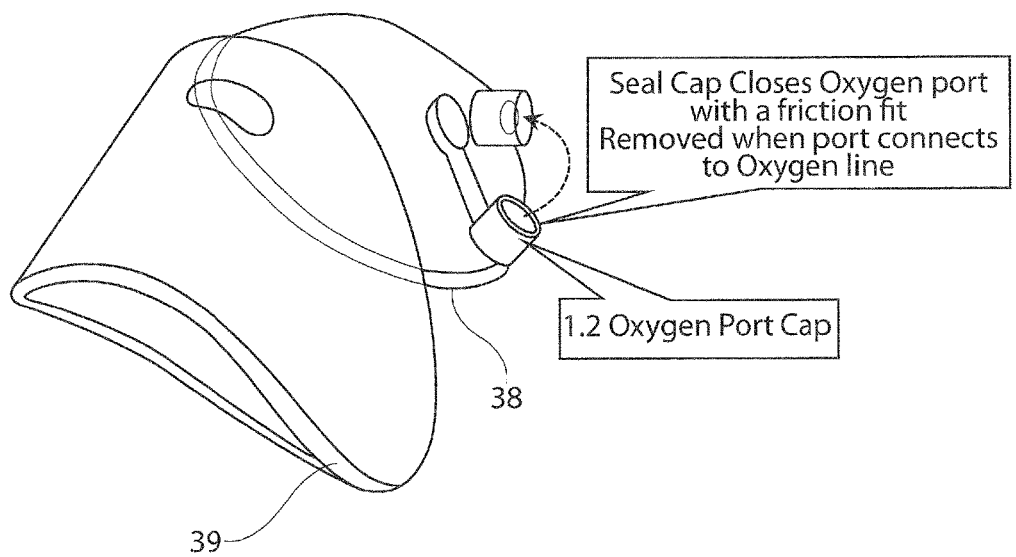
FIG. 5 is a perspective view of the nasal chamber portion of FIG. 1.

Major elements of mask 10 in accordance with the present invention are illustrated FIGS. 1-5. The primary elements of the mask are a nasal chamber 12 and an oral chamber 14. Nasal chamber 12 is the primary structural element of the mask supporting all other sub-elements of the mask as will be described below. When combined as illustrated in FIG. 1 and FIG. 2, gases from the ventilator or to the ventilator are passed through both the mouth and the nose. The mask 10 operates as a traditional full face ventilation mask in this configuration. The full mask provides gases to the patient and removes waste gas through a ventilation port of the nasal chamber which attaches to a ventilation circuit that then attaches to an anesthesia machine. Gases can be exchanged from the patient's nasal orifice and or the oral orifice of the patient. One or more duckbill valves 16 are integral to the nasal chamber 12 as shown in FIG. 2D. In this state, they seal the nasal chamber 12, preventing flow out of the valve orifices. When the distal end of the oral chamber 14 proboscis tube 18 is engaged with the duck bill valve 16 located in the nasal chamber 12, the valve is opened, allowing gas transfer between the nasal and oral chambers. A duck bill valve separated from the nasal chamber 12 but placed on the oral chamber hollow proboscis tube is shown in FIG. 2E to illustrate how the valve is opened when the proboscis tube is engaged. The seal of the nasal chamber surrounds the nose and with the duck bill valves closed, gas exchange can only occur between the nose and the ventilation port, being contained by the other elements of the chamber.

The nasal chamber 12 and oral chamber 14 of the mask are mated and connected to one another through a nasal/oral port 17 which includes a septum or duck valve 16 (FIG. 2A-2E). Alternatively, as shown in FIG. 3, nasal chamber 12 and oral chamber 14 may be mated and connected to one another through nasal/oral port 17 by a tapered proboscis 18 which extends from the oral chamber 14 and engages with a tapered port 20 in the nasal chamber 12. A snap cap 22 which may be held on a line retainer 24 or hinged to a retainer ring 26 is provided for sealing port 20 when the nasal chamber 12 and oral chamber 14 are separated from one other.

Figure 6:
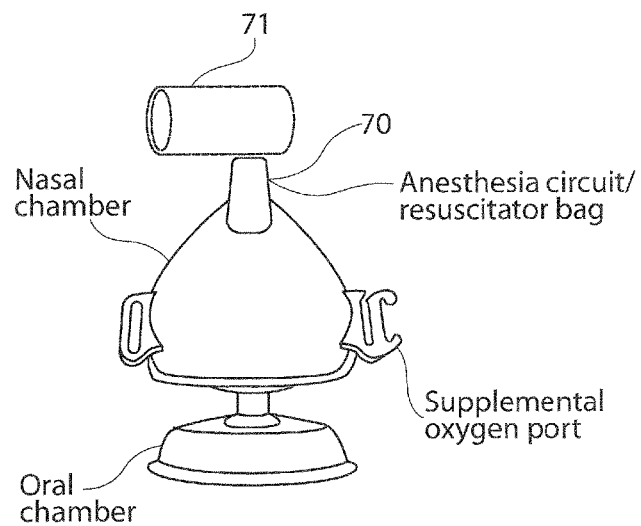
FIG. 6 is a view similar to FIG. 1 of an alternative embodiment of mask in accordance with the present invention.

A nominal, e.g., 15 mm diameter OD ventilator port 28 in the nasal chamber 12 interfaces with an anesthesia ventilation circuit or bag-mask (not shown). A preferred orientation of the ventilator port 28 is on the left side of the mask although alternate positions could be off center or on the right side of the mask as illustrated in FIG. 6. When a patient is being transported, the ventilation port 28 remains open to the atmosphere, and allows $CO_2$ and other gasses to escape the patient during the breathing process.

A second port 30 for introduction of oxygen is provided in nasal chamber 12, and includes a cap 32 which seals the oxygen port 30 during ventilation of the patient. Cap 32 is removed during patient transport and an oxygen supply line (not shown) is connected to the oxygen port 30, and typically past operation. The connection can be either a "Christmas Tree" type, as the preferred style, or a luer lock connection. The preferred location of oxygen port 30 is on the left side of the patient. An alternate configuration could be on the right side.

When the nasal chamber 12 and oral chamber 14 are connected, the septum valve 16, is opened by the septum valve proboscis 18. This opening allows gas flow between the nasal chamber 12 and the oral chamber 14. As noted supra, a septum or duck valve is the preferred configuration, although other valves that are open when the two chambers are connected are possible. When the two chambers are separated, the proboscis 18 is removed, the duck valve 16 closes, sealing the nasal chamber 12 and prevents flow of gas out of the nasal chamber due to ventilator pressure inside the chamber. One or more septum or duck valves can interface between the nasal chamber 12 and the oral chamber 14, although, two are a preferred configuration. Alternatively, simple caps or plugs may be used in place of the septum or duck valve(s) to seal the nasal chamber. Note that in an alternate configuration the separate oxygen port 30 may be eliminated, and the oxygen supply line could interface directly with nasal portion of the nasal/oral port 17. A snap cap interface 34 exists on the outside of oxygen port 30. During nasal ventilation, a snap cap 36 is placed over oral port 30, sealing the nasal chamber 12. When the nasal chamber 12 and oral chamber 14 are connected, the tapered nasal/oral proboscis 18 engages with the nasal/oral port 17, creating a seal to the exterior, while allowing gas flow between the nasal chamber 12 and oral chamber 14. Note that in an alternate configuration, the duck valve or septum port could be located on the oral chamber 14 and the hollow proboscis located on the nasal chamber 12.

Anchor straps 38, 40 are located on the left and right sides of the nasal chamber 12. Anchor straps 38, 40 secure the mask to a patient's head or to a patient head support device as described in our PCT application number PCT/US 14/44934, or in our U.S. Application Ser. No. 62/118,301, filed Feb. 19, 2015, the contents of which are incorporated herein by reference.

Soft interface rings 38, 39, which may be, e.g. a gel filled or air filled ring, or ring formed of a low durometer material such as foam, silicone, a low durometer thermoplastic elastomer, a low durometer thermoplastic urethane, are connected to the nasal chamber 12 and oral chamber 14, and interface the nasal chamber 12 and the oral chamber 14, respectively to the patient's face over the nose and mouth, providing near-air-tight seals, as will be described in detail.

When the nasal chamber 12 solely is being used for ventilation of a patient, the nasal/oral port is sealed it so that positive ventilation pressure can be achieved.

Use of the nasal/oral mask of the present invention will now be described. When the nasal chamber 12 and oral chamber 14 of the mask are connected as shown in FIG. 1, the mask is a full face ventilation mask. Both the nasal and oral openings of a patient's face are in communication with the ventilator circuit.

When the nasal chamber 12 and oral chamber 14 of the mask are separated as shown in FIG. 3, the mask may be used solely as a nasal ventilation mask. Providing nasal ventilation allows for oxygenation to occur even during intubation or while performing bag-mask ventilation. Note that alternate configurations of the mask could consist of the nasal chamber 12 only, with no septum valve or oral chamber being included in the configuration.

Ventilation port 28 as shown is designed to nominally fit on the inner diameter of a ventilation circuit (not shown). Alternate configurations are possible where the ventilation port 28 fits the outer diameter of the ventilation circuit. In use, ventilation port 28 is connected to a anesthesia circuit, while the oxygen port 30 is connected an $O_2$ supply. The ventilation port 28 may be located to the top or to one side of the mask (preferably to the left side of the mask). In the FIGS. 1-5 embodiment, the oxygen port 30 is located to one side, preferably to the left side of the mask (from the anesthesiologist's viewpoint), so as to permit laryngoscopy and intubation to be viewed by the anesthesiologist from the right side of the patient's face, and not obstruct the anesthesiologist's view of the patient's oral cavity. Of course, the ventilation port 28 and oxygen port 30 may be located on the right side of the mask as well (from the anesthesiologist's viewpoint).

In another embodiment, shown in FIG. 6, a ventilation port 70 may project off center from the nasal chamber 12 as a straight port or angled to the right side of the nasal chamber (shown in phantom at 71) nominally located in the X-Y plane located on the right side of the patient, projecting in a negative X direction that can be parallel to the X axis. The angle of the port relative to the X axis can project at an angle that varies from plus 90 degrees to negative 90 degrees. In another alternative embodiment ventilation circuit port, 70, may be provided projecting from the top of the nasal chamber 12 in the negative Y direction as an elbowed port. The open end of the elbowed port 70 that connects with the ventilator may be oriented to point to the right side of the patient projecting in the positive X direction that can be parallel to the X axis. The angle of the elbowed port relative to the X axis can project at an angle that varies from plus 90 degrees to negative 90 degrees.

In still yet another embodiment ventilation port 70 may project from the top of the nasal chamber 12 in the negative Y direction as an elbowed port nominally located in the X-Y plane. In such embodiment, the open end of the elbow that connects with the ventilator points to the left side of the patient projecting in the negative X direction that can be parallel to the X axis. Additionally the angle of the elbowed port relative to the X axis can project at an angle that varies from plus 90 degrees to negative 90 degrees.

The angle of the elbow portion of the alternate ventilation port, 70 that is nominally located in the X-Y plane also can project to an angle out of that plane by plus 90 degrees to negative 90 degrees.

Oxygen port 30 may project from the side of the left nasal chamber as a straight port nominally located in the X-Y plane located on the left side of the patient projecting in the negative X direction that can be parallel to the X axis. The angle of oxygen port 30 relative to the X axis can project at an angle that varies from plus 90 degrees to negative 90 degrees. Oxygen port 30 may project from the side of the nasal chamber 12 as a straight port nominally located in the X-Y plane located on the right side of the patient projecting in the positive X direction that can be parallel to the X axis. Additionally the angle of the oxygen port 30 relative to the X axis can project at an angle that varies from plus 90 degrees to negative 90 degrees. Oxygen port 30 also may project from the top of the nasal chamber 12 in the negative Y direction as an elbowed port nominally located in the X-Y plane. The open end of the elbow that connects with the ventilator points to the right side of the patient projecting in the positive X direction that can be parallel to the X axis. Additionally the angle of the elbowed port relative to the X axis can project at an angle that varies from plus 90 degrees to negative 90 degrees.

Oxygen port 30 also may project from the top of the nasal chamber in the negative Y direction as an elbowed port nominally located in the X-Y plane as shown in phantom in FIG. 3 at 30A. The open end of the elbow that connects with the ventilator is pointing to the left side of the patient projecting in the negative X direction that can be parallel to the X axis. Additionally the angle of the elbowed port relative to the X axis can project at an angle that varies from plus 90 degrees to negative 90 degrees.

Figure 7:
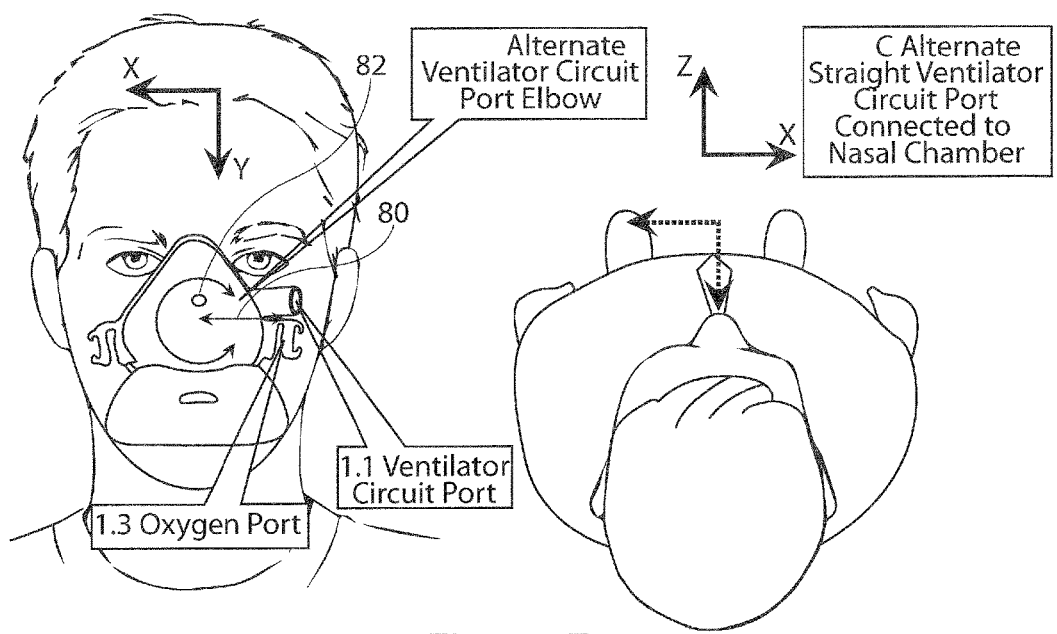
FIG. 7 is a view similar to FIG. 1 of another alternative embodiment of mask in accordance with the present invention.
Figures 8A, 8B, 8C:
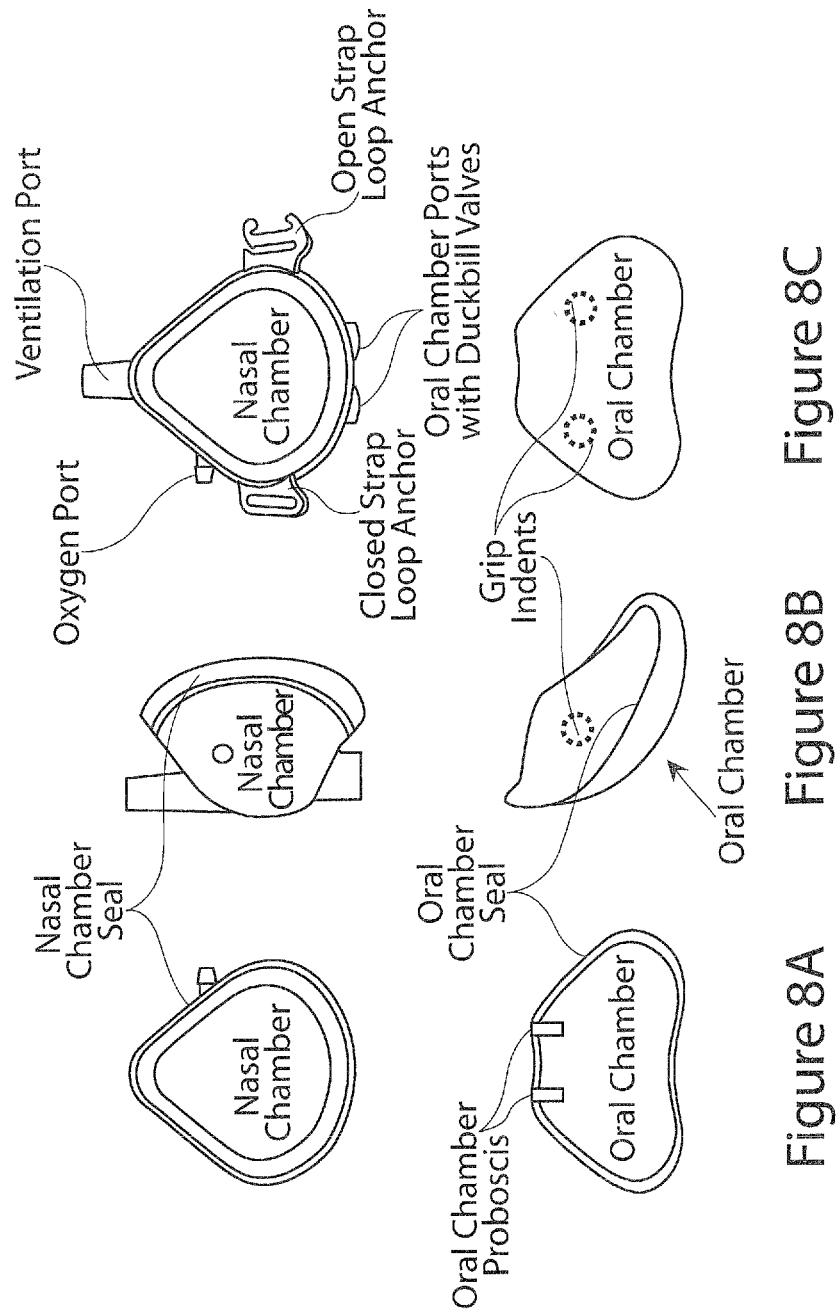
FIG. 8A is an exploded view from the interior of a combined nasal mask and oral mask in accordance with the present invention.
FIG. 8B is an exploded side elevational view of a combined nasal mask and oral mask in accordance with the present invention.
FIG. 8C is an exploded front view of a combined nasal mask and oral mask in accordance with the present invention.
Figure 13F:
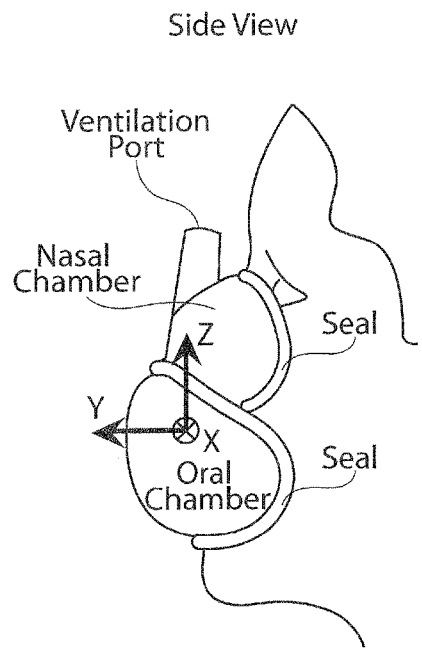
Figure 13G:
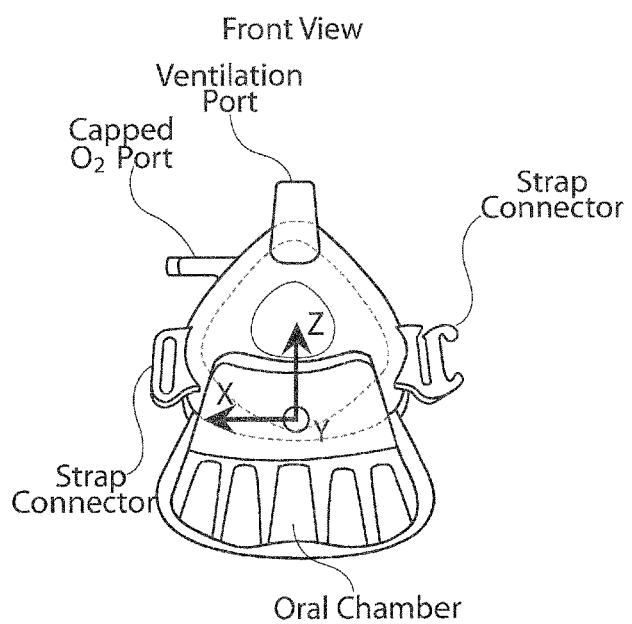

Yet another alternative is shown in FIG. 7, where the ventilation port 80 projects from the front of the nasal chamber 12 in the positive Z direction as an elbowed port which, in a preferred embodiment is swivel mounted. The open end of the elbow that connects with the ventilator points to the left side of the patient projecting in the negative X direction that can be parallel to the X axis as shown in FIG. 13, nominally in the X-Y plane. Additionally the angle of the elbowed port relative to the X axis can project at an angle that varies from plus 180 degrees to negative 180 degrees. The angle of the elbow portion of the alternate ventilation port 80 that is nominally located in the X-Y plane also can project to an angle out of that plane by plus 90 degrees to negative 90 degrees. An oxygen port also may project from the front of the nasal chamber 12 in the positive Z direction as an elbowed port 82. The open end of the elbow that connects with the ventilator is pointing to the left side of the patient projects in a negative X direction that can be parallel to the X axis as shown in FIG. 13, nominally in the X-Y plane. Additionally the angle of the elbowed port relative to the X axis can project at an angle that varies from plus 180 degrees to negative 180 degrees. The angle of the oxygen port elbow 82 portion that is nominally located in the X-Y plane also can project to an angle out of that plane by plus 90 degrees to negative 90 degrees.

Alternatively, the ventilation port 28 may project from the side of the nasal chamber as a straight port nominally located in the Y plane located in the front of the nasal chamber 12 projecting in the negative y direction, and the oxygen port 30 project from the side left of the nasal chamber as a straight port nominally located in the X-Y plane located on the left side of the patient projecting in the negative X direction that can be parallel to the X axis. Additionally the angle of the ventilation and oxygen ports relative to the X axis can project at an angle that varies from plus 90 degrees to negative 90 degrees.

Referring again to FIG. 7, the ventilation port 80 may project from the front of the nasal chamber 12 in the positive Z direction as an elbowed port. The elbow has the ability to swivel 360 degrees about the Z axis of the straight port connected to the nasal chamber as illustrated. This allows 360 degree access of the ventilator circuit to the mask. This swivel elbow is nominally a 90 degree elbow but could be any angle. Additionally the straight ventilator port connected to the nasal chamber could also be in any location as suggested earlier on the chamber.

Views of the nasal and oral chambers and corresponding seals are shown in FIGS. 8A-8C and FIGS. 9A-9F. As can be seen in the drawings, the seals 102, 104 are attached along the nasal and oral chambers 106, 108 perimeter. As described above, the nasal chamber 106 has a ventilation port 110 that attaches to the ventilation circuit, an oxygen port 112 that attaches to an oxygen source and two oral chamber ports 114, 116 with duckbill valves that are closed when the oral and nasal chambers are disengaged. The nasal chamber 106 also has closed and open strap loop anchors 118, 120 where a strap 122 attached on either side and circles the back side of the patient's neck (see FIG. 10), securing the mask to the patient with a tension force $F_{Tension}$. The oral chamber 108 has two proboscis 124, 126 that engage with the oral chamber ports 114, 116 opening the duckbill valves, so that both the oral and nasal chambers 106, 108 are at the same pressure level as determined by the ventilation circuit attached to the ventilation port.

In the illustrated embodiment, the nasal chamber is intended to seal, in part to the oral chamber. Alternatively, as will be described below, the nasal chamber and the oral chamber may be sealed directly and independently to the patient's face, in which case a Y-shaped seal is the preferred seal for both chambers. The seals are intended to keep gases within the chambers when pressurization is provided via the ventilation port. In this embodiment are two types of seals 102, 104 in the mask, a multi-lobed, preferably Y-shaped seal 102 (Y describes the seal cross-section) which is the interface between the oral chamber 108 and nasal chamber 106 to the face of the patient, and a J-shaped seal 104 (J describes the seal cross-section) which is the interface between the region where the oral and nasal chambers 108, 106 connect. In both cases, the intent of the seal is to prevent gas from leaving the chamber through those interfaces when the chambers are pressurized relative to the ambient environment.

Figure 11A:
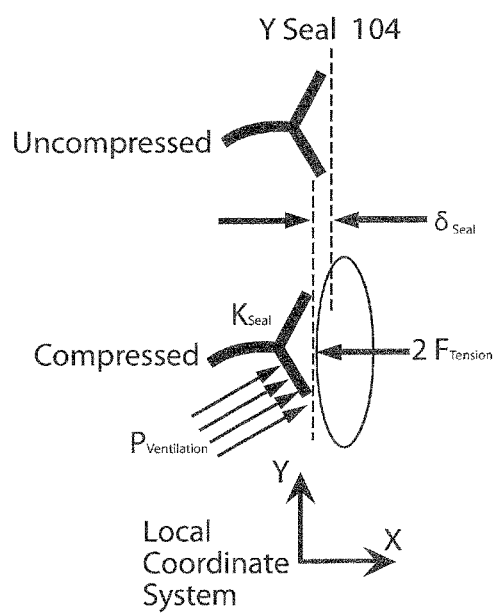
FIGS. 11A and 11B show details of the Y element of the combined nasal mask and oral mask in accordance with the present invention.
Figure 11B:
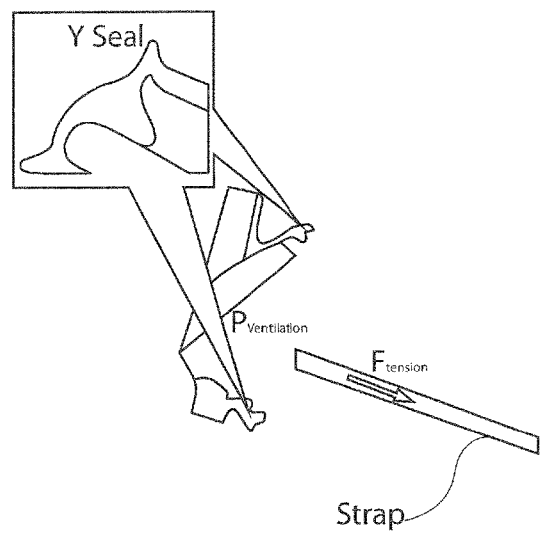

Details of the force and pressure interaction of the multi-lobed, preferably Y-shaped seal with the patient's face are illustrated in FIGS. 11A-11B. The base of the multi-lobed, preferably Y-shaped seal 104 is attached to the chamber parallel to the local X axis. In this case, the nasal chamber is shown. When the tension force of the strap, $F_{Tension}$, is applied on the right and left side of the patient's face, the multi-lobed, preferably Y-shaped seal is compressed as illustrated, reacting to the force applied by the strap. The multi-lobe, preferably Y-shaped seal is made of a pliable elastomer and the cantilever of the Y provides an effective spring stiffness, $K_{Seal}$. The seal will compress by an amount $\delta_{Seal}$ when the strap tension force is applied. The resulting force balance for the mask can then be described as in FIGS. 11A-11B.

$$K_{seal} \times \delta_{Seal} = 2 \times F_{Tension}$$

An additional benefit of the multi-lobed, preferably Y-shaped seal design is that when a differential pressure, $P_{Ventilation}$, is applied to the interior of the chamber as illustrated in FIG. 11A, the seal is forced against the skin, making it more difficult for the gas to flow between the seal and the skin due to the resulting force applied to the interior Y arm of the seal, pushing it against the skin.

Details of the J-shaped seal 102 (J describes the seal cross section) are illustrated in FIGS. 12A-12D. Note the interior of the J-shaped seal 102 is attached to the oral chamber in the region that interfaces with the nasal chamber when the two chambers are engaged. The J-shaped seal 102 is made of an elastomer with an effective spring stiffness $K_{JSeal}$. When the nasal and the oral chambers are engaged, a force, $F_{JSeal}$ is applied and the seal is compressed by an amount $\delta_{Seal}$. Note the J portion of the seal points inward towards the pressure as illustrated in FIG. 12C provided by the ventilation circuit $P_{Ventilation}$. The relationship between the applied force and displacement can then be stated as follows:

$$K_{JSeal} \times \delta_{JSeal} = F_{JSeal}$$

As will be appreciated, the multi-lobed, preferably Y-shaped seal and the J-shaped seal provide numerous advantages. For one the multi-lobed, preferably Y-shaped seal prevents gas leaving the pressurized portion of the oral and/or nasal chamber of the mask. Also, the multi lobe, preferably Y-shaped seal, when pressurized, the interior leg of the Y is pressed against the patient's face, further sealing the mask. And the J-Seal seals the oral chamber and nasal chamber interface when the two chambers are engaged, preventing gas from escaping through that interface. Further, the J-Seal, when pressurized, the interior hook of the J is pressed against the patient's face, further sealing the mask. Moreover, the multi-lobed preferably Y-shaped seal on the nasal chamber over-laps the J-shaped seal of the oral chamber, preventing gas from escaping that interface when both chambers are pressurized.

With the mask of the present invention duckbill valves are closed when the oral and nasal chambers are separated, and open when engaged by the proboscis of the oral chamber, allowing gas flow between the oral and nasal chambers.

Finally, grip indents are provided on the left and right surfaces of the oral chamber allowing easier gripping by the anesthesiologist in placing the mask onto a patient's face.

FIGS. 13A-13E provide side, rear, interim and front views of still yet embodiment of a combined nasal and oral mask made in accordance with the present invention. In this embodiment the nasal and the oral chambers individually seal to the patient's nose and mouth, respectively, and a seal between the nasal and oral chambers occurs at the proboscis—duck bill valve interface shown in FIGS. 13A-19B. This allows the nasal and oral chambers to move relative to one another and still maintain a seal over the mouth and nose so long as the proboscis and duck bill valves remain engaged. Another benefit is that the oral and nasal chambers can translate and rotate about the X, Y and Z axes relative to each other due to flexibility of the proboscis—duck bill valve configuration, prior to being mated together. The proboscis tubes are inserted into the duck bill valves, opening them when the two chambers are engaged.

More particularly a full face ventilation mask consisting of an oral chamber and a nasal chamber is illustrated in FIGS. 13A-13F. The full mask provides gases to the patient and removes waste gas through the ventilation port of the nasal chamber that is highlighted. This port attaches to a ventilation circuit that then attaches to an anesthesia machine. Gases can be exchanged from the patient's nasal orifice and or to the oral orifice of the patient in this configuration.

Figure 14A:
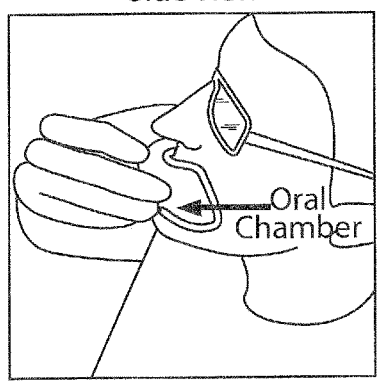
Figure 14C:
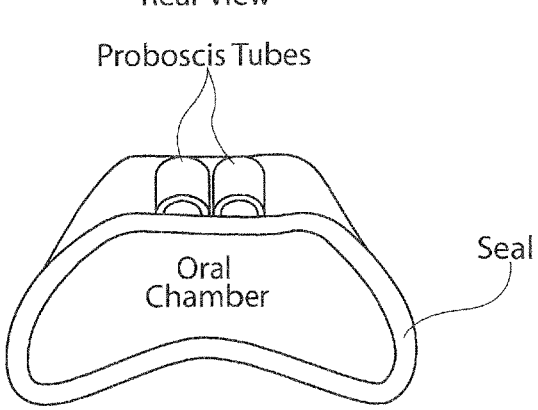
Figure 14B:
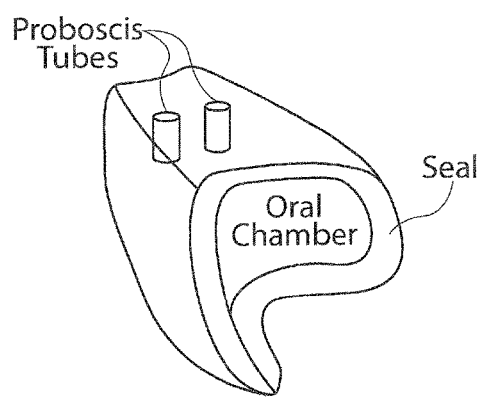
Figure 15A:
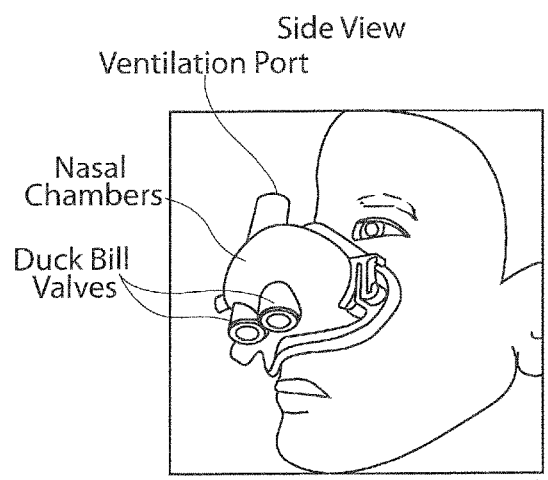
Figure 15B:
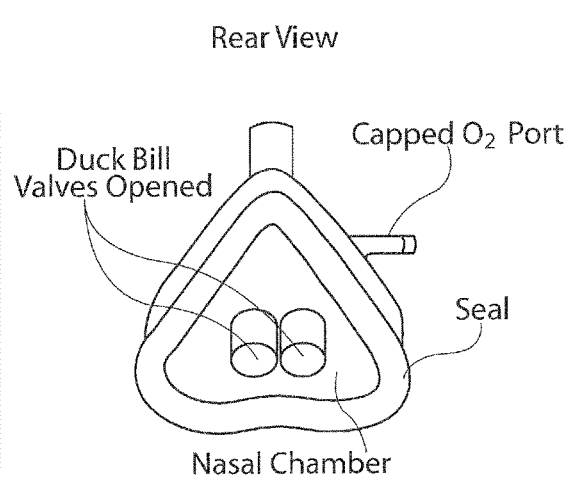
Figure 15C:
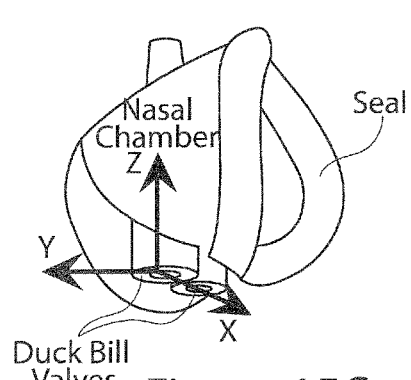
Figure 15D:
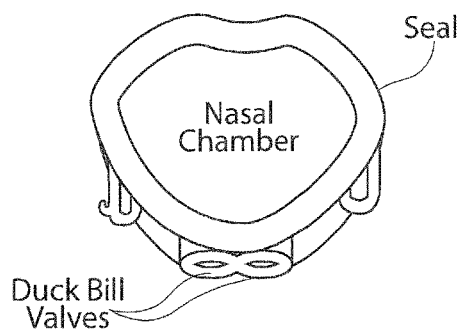

The oral chamber portion of the mask is shown in FIGS. 14A-14C. The oral chamber consists of the chamber, "Y" a seal that surrounds the chamber opening and one or more proboscis tubes (two tubes are shown in this configuration). The chamber seal surrounds the mouth of the patient, sealing the chamber to the patient's mouth so that gas exchange through the mouth can only occur through the proboscis tubes as shown in FIGS. 14B and 14C.

The nasal chamber portion of the mask shown in FIGS. 15A-15D consists of the nasal chamber, a "Y" seal that surrounds the perimeter of the chamber, one or more duck bill valves, an $O_2$ port and a sealing cap over the $O_2$ port. The seal of the nasal chamber surrounds the nose and with the duck bill valves closed, as is the case in this configuration, gas exchange can only occur between the nose and the ventilation port, being contained by the other elements of the chamber.

Figures 16A, 16B:
Figure 16C:
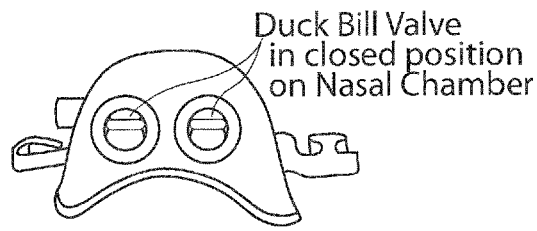
Figure 17:
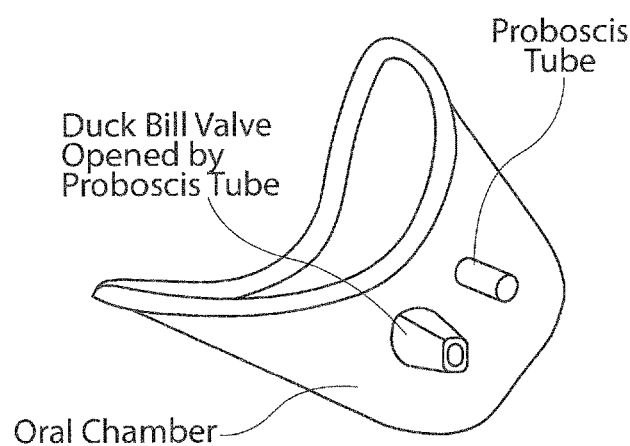

One or more self-closing valves, preferably in the form of duckbill valves are integral to the nasal chamber as shown in FIG. 12C. When the nasal chamber and oral chamber are separated, the valves seal the nasal chamber, preventing flow out of the valve orifices. Views of the duck bill valve separate from the chamber and integrated into the chamber is shown in FIGS. 16A-16B. When the proboscis of the oral chamber proboscis tube is engaged with the duck bill valve located in the nasal chamber, the valve is opened, allowing gas transfer between the nasal and oral chambers. A duck bill valve separated from the nasal chamber but placed on the oral chamber hollow proboscis tube is shown in FIG. 17 to illustrate how the valve is opened when the proboscis tube is engaged.

FIGS. 18A-18B provides side and rear views of the nasal and oral chambers prior to being engaged as a full face ventilation mask assembly. The proboscis tubes of the oral chamber are inserted into the duck bill valves of the nasal chamber, opening them when the oral and nasal chambers are engaged.

When the nasal and oral chambers are engaged as illustrated in FIGS. 19A-19C, gas exchange between the two chambers can occur via the hollow proboscis tubes and the open duck bill valves.

The embodiment shown in FIGS. 13A-19B provides several advantages:

- the nasal chamber when used by itself, seals over the nose, allowing gas exchange between the nasal cavity and a ventilation machine via a ventilation port;
- the oral chamber seals over the mouth, allowing gas exchange to the atmosphere or to the nasal chamber via the hollow proboscis tubes;
- the engaged nasal and oral chambers separately seal the nose and mouth respectively, and allow gas exchange between the two chambers via the proboscis tubes and opened duck bill valve;
- the engaged nasal and oral chambers allow gas exchange via the ventilation port of the nasal chamber and the anesthesia machine; and
- the engaged nasal and oral chamber have an ability to move relative to each other to better fit patients and seal around the nose and nasal chamber and mouth and oral chamber respectively, due to the flexibility of the proboscis engaged with the duck bill valve in translation or rotation about the X, Y and Z axes.

The mask of the present invention has numerous advantages over prior art masks. These include:

- it can be used as both a nasal and mouth anesthesia mask for bag-mask ventilation;
- it can be used as a nasal mask alone for bag-mask ventilation. In such case, the $O_2$ port 30 should be capped with the cap plug 36 in order to prevent gas from exiting the $O_2$ port. This same configuration of course could be used when the nasal mask alone is connected to a ventilation machine;
- it can be used as both a full face nasal and mouth anesthesia mask for the delivery of anesthetic gases or for delivery of supplemental $O_2$;
- it can be used as a nasal mask alone for the delivery of anesthetic gases or for delivery of supplemental $O_2$;
- it can be used for nasal CPAP or for full face mask CPAP;
- it can be used for nasal CPAP or for full face mask CPAP to relieve upper airway obstruction due to the relaxation of upper airway soft tissue from intra-venous or inhalation anesthetics;
- it can be used for nasal CPAP or for full face mask CPAP to relieve upper airway obstruction in patients with obstructive sleep apnea;
- it can be used to deliver oxygen and for ventilation during apneic periods (i.e., induction of anesthesia and paralysis during induction of anesthesia) via nasal mask without interfering with endotracheal intubation;
- it is transparent, at least in part, which enables the anesthesiologist to visualize condensation or aspiration;
- it has separate but attachable and detachable nasal and mouth masks;
- it is both an anesthesia nasal and mouth mask with a head strap that secures the patient's head and neck in position to maintain an open airway;
- it is an anesthesia nasal mask with a head strap that secures the patient's head and neck in position to maintain an open airway;
- it is both an anesthesia nasal and mouth mask with a head strap that secures the patient's head and neck in position hands free; and
- it is an anesthesia nasal mask with a head strap that secures the patient's head and neck in position hands free.

Referring to FIGS. 20A-20E, to utilize the nasal portion of the mask for Continuous Positive Airway Pressure (CPAP), or to utilize the combination nasal and oral mask for full face mask CPAP, the ventilation port must be plugged or capped and pressurized oxygen must be supplied to the mask via the $O_2$ port. FIG. 20A shows the mask with the $O_2$ port 30 capped by a cap plug 400 on the right; the cap plug is removed from the $O_2$ port and the cap plug 400 is utilized to partially or completely plug the ventilation port 28 in FIGS. 20B and 20C. Referring in particular to FIGS. 20D and 20E, the cap plug 400 includes an interior recess 402 sized and shaped to fit snuggly over the $O^2$ port 404. Cap 400 is attached to the mask by a tether 406. When mounted on the $O_2$ port, the cap covers and seals the $O_2$ port, preventing any gases from leaking out of the mask. Cap plug 400 has one or more generally V-shaped grooves 408 on a periphery wall of the cap plug 400. Grooves 408 preferably vary in width, $W(y)$ as a function Y as in Equation 1. This is one of multiple examples where the width varies as a function of Y. Conversely the depth D could vary as a function of Y. The area open between the nasal chamber and ambient atmosphere, $A(Y)$ for each groove in the region between the valve and the ventilation port is determined by Equation 2 where:

$$W(Y)=W_1-(W_1-W_2)/L \times Y \qquad \text{Equation 1}$$

$$A(Y)=W(Y) \times D(\text{per groove}) \qquad \text{Equation 2}$$

For this arrangement rate of flow out of the ventilation port can be controlled by the amount the cap plug is inserted into the ventilation port as shown in FIG. 20B. A pressurized $O_2$ line is also attached to the $O_2$ port 30 in the FIG. 20B. The configuration shown in FIGS. 20B and 20C allows for the controlled application of CPAP. With the ventilation port capped, the nasal chamber remains pressurized, and gasses exit the system by having the patient exhale through the mouth.

Figure 21:
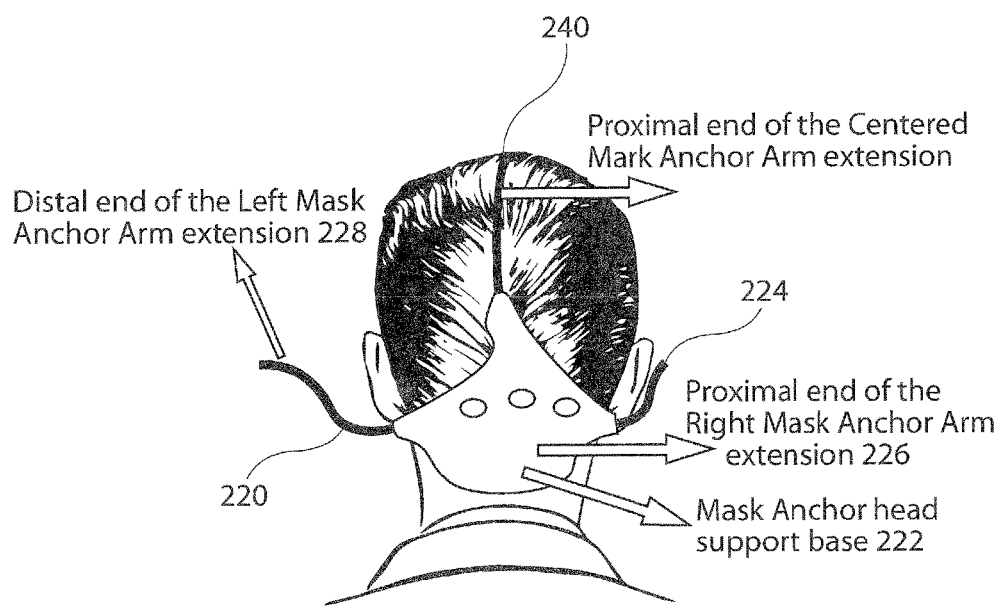
FIG. 21 is an end view showing a mask anchor applied to the head of a patient.
Figure 22:
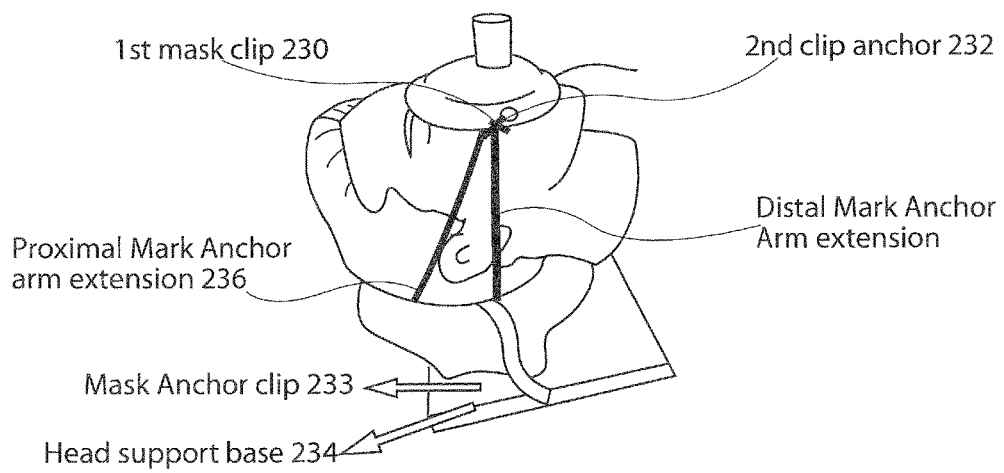
FIG. 22 is a side elevational view thereof.

Referring to FIGS. 21 and 22, there is illustrated a head strap device 20 which comprises a head bonnet 222, which comes in contact to the back of the patient's head and one or more arm extensions 224, which contains both a proximal arm extension 226 with two ends and a distal arm extension 228 with two ends. The first end of the proximal arm extension 226 is attached to the head bonnet 222 and the second end of the proximal arm extension 228 is provided for attachment to a mask clip 230. The mask clip 230 allows the distal arm extension 228 of the head support head strap to attach and prevents the arm extensions 224, 226 from coming undone. The first end of the distal arm extension 228 attaches to the mask clip 230 alone to create a seal or can attach to both the mask clip 230 and a anchor clip 233 to secure the patient's head to a surface 234 such as the operating table or head support base, and prevent the patient's head from moving. The mask anchor clip 232 allows the distal arm extension 228 of the head strap to attach at a second point which reinforces it and further prevents the arm extension 228 from coming undone.

The mask clips 230, 232 have several functions. First they allow for a third attachment for the distal arm extensions 228 of the head strap to prevent the distal arm extensions 228 from coming undone. A second function is to prevent a patient's head from moving side to side by securing the patient's head to the head support surface 234. When the distal arm extensions 228 of the head strap attach to the mask clips 232, it secures the patient's head to the surface 234.

Figure 23:
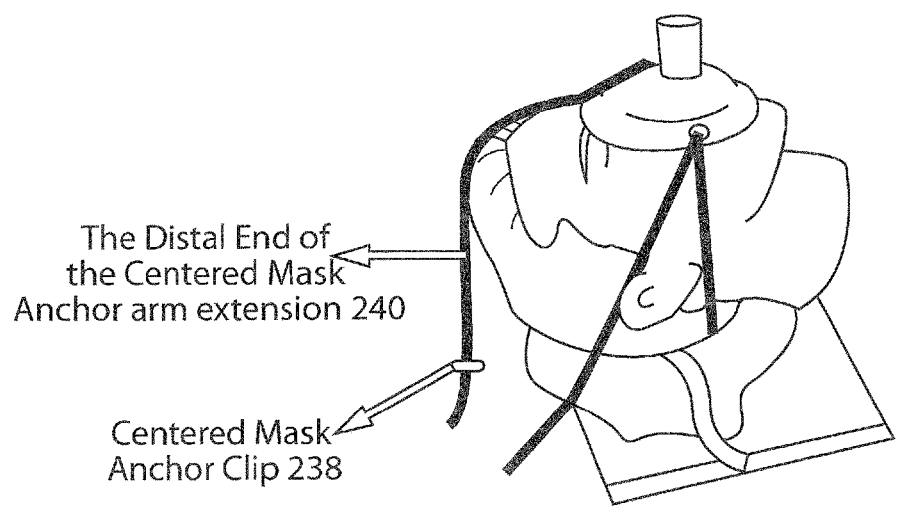
FIG. 23 is a perspective view thereof.

A third function of the mask anchor clip 232 is to prevent the patient's head and/or neck from moving away from the head support 234 or head support pillow 236 when the head and/or neck angles of the patient are adjusted. The distal end of the mask arm extension 240 (FIG. 23) attaches to a centered mask anchor clip 238 and acts as a posterior head strap that not only prevents the patient's head from moving, but it also maintains the patient's head position relative to the head support pillow 236 when the head support angle is being changed. The centered mask anchor clip 238 enables the distal end of the centered mask anchor arm extension to attach and prevent the patient's head from moving both side to side and relative to the head support pillow 236 when the head support angle is changed.

Figure 24A:
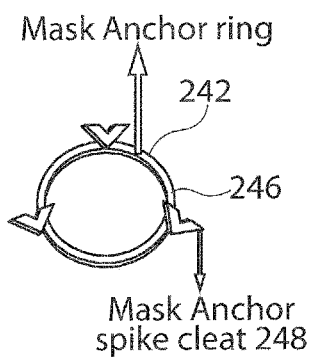
FIG. 24A is a top-plan view of a mask anchor ring in accordance with further embodiment of the invention.
Figure 24B:
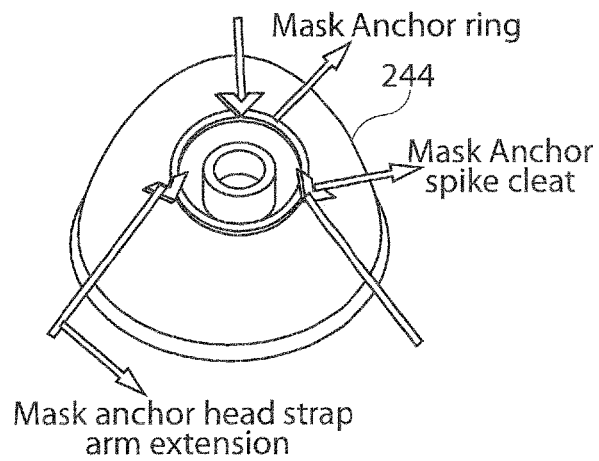
FIG. 24B is a view similar to FIG. 24A showing a mask anchor ring on a mask.

In another embodiment the mask anchor head strap attaches to the mask anchor ring 242, which can be placed over an aperture 244 of a mask and surrounds the aperture 244 of a mask, rather than attach directly to the clips built into the mask (FIGS. 24A and 24B). The mask anchor ring consists of two sides, a first rigid base 246, which comes in contact and rests on the mask and a second rigid side, which has one or more attachments (mask anchor spike cleats 248) for the head straps to attach to and create a seal.

The mask ring has an advantage in that it can be used with different size masks. Also, if desired, two or more straps may be placed on each side of the mask.

Figure 25A:
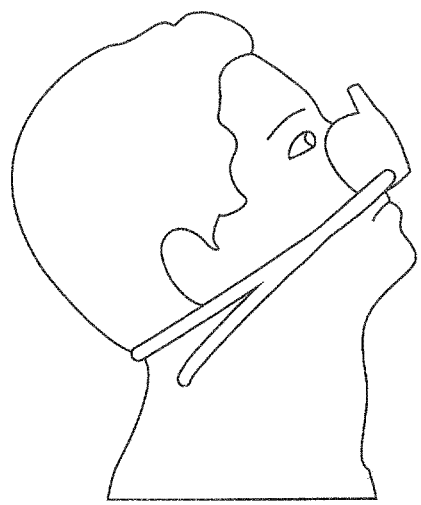
FIGS. 25A and 25B depict a ventilation mask on a patient in the sniff position (FIG. 25A) and in a natural or "vertical" position (FIG. 25B)
Figure 25B:
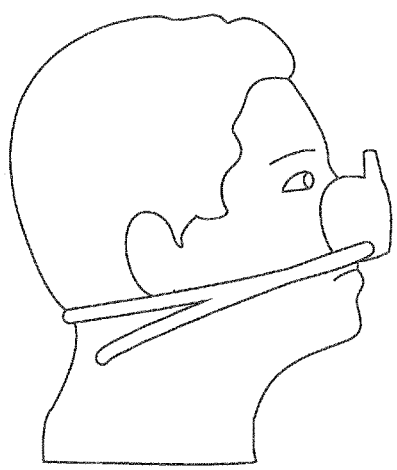

Referring now to FIGS. 25A and 25B, in yet another aspect of the present invention provides a ventilation or anesthesia mask strap system designed to remain in tension, maintaining the mask position on the patient by pulling the mask against the face, while a patient is in the Sniff Position as illustrated in FIG. 25A, and post operation when the patient's head is in a natural or "vertical" position illustrated in FIG. 25B. In order to maintain strap tension, the total strap elongation when placed on the patient must be greater than ($L_{Sniff}-L_{Vertical}$). The issue is that when $L_{Sniff}$ is greater than $L_{Vertical}$ and if the elongation is less than the difference, the strap will no longer be in tension.

Figure 26A:
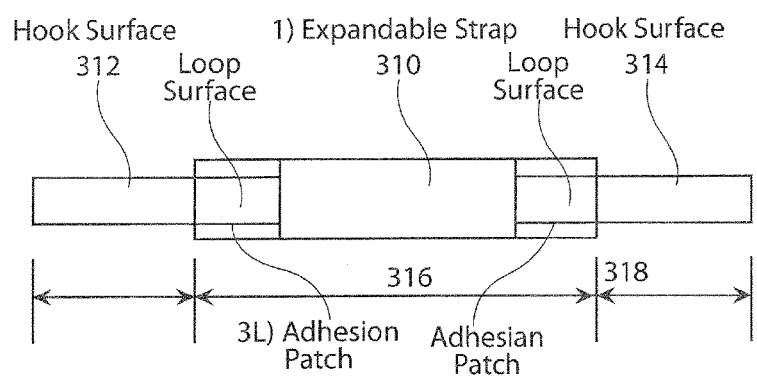
FIGS. 26A and 26B are top plan and side elevational views, respectively of a ventilation mask strap system in accordance with the present invention.
Figure 26B:
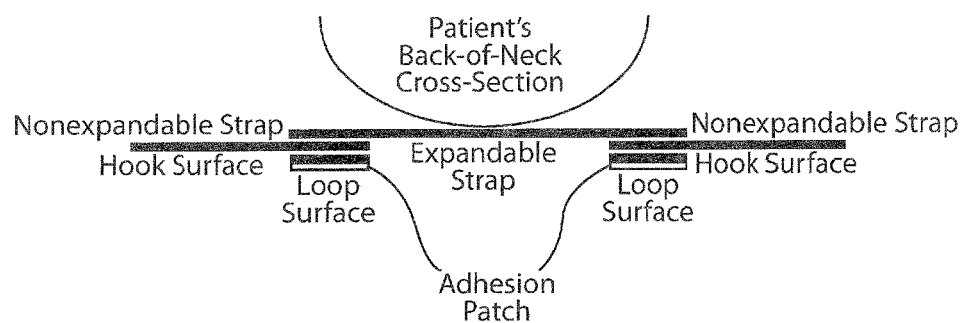

An outer and top view of the strap, along with its major elements, are illustrated in FIGS. 26A and 26B. These elements include an expandable strap section 310, which has the ability to extend up to twice its length, or more, when a tension force is applied to the left and right end.

A first non-expandable strap section 312 is positioned on the left side of the patient with a hook surface on the strap outer side, away from the patient's neck, and is attached to the expandable strap on the outer or inner side of the expandable strap. A second non-expandable strap section 314 is positioned on the right side of the patient with a hook surface on the strap outer side, away from the patient's neck, and is attached to the expandable strap on the outer or inner side of the expandable strap. A first hook and loop adhesion patch 316 is positioned on the left side of the patient with loop surface on the strap outer side, away from the patient's neck that is attached to the expandable strap on the outer most surface. A second hook and loop adhesion patch 318 is positioned on the right side of the patient with loop surface on the strap outer side, away from the patient's neck that is attached to the expandable strap on the outermost surface. Alternatively, the loop and hook surfaces could be reversed on the nonexpendable strap sections and adhesion patch accordingly. Alternatively, the non-expandable strap sections and the expandable strap section may be fixed to one another by an adhesive or mechanically such as by buttons, staples, stitching, snaps, etc.

FIGS. 27A and 27B provide top and outer views of a strap attached to a ventilation mask in accordance with the present invention. The left and right non-expandable strap sections 312, 314 are threaded through strap interfaces 320, 322 on the left and right side respectively of the mask 324. The left and right non-expandable straps 312, 314 are attached to the respective left and right adhesion patches 316, 318. The surface of the non-expandable strap has a hook surface and the adhesion patch has a loop surface. The surfaces could be reversed where the non-expandable strap has the loop surface and the adhesion patch the hook surface.

In use the mask 324 is placed over patient's nose and the strap is drawn around the back of the neck as shown in FIG. 25A. The left and right non-expandable straps are pulled away from the patient's neck, creating tension when the expandable strap 310 extends or stretches due to the force applied by the anesthesiologist. They are then inserted through the strap interfaces 320, 322 back towards the patient's neck and attached to the hook & loop interface at the left and right adhesion patches 316, 318, respectively, creating strap loops 326, 328 as illustrated in FIG. 27A. The tension, resulting from the extension of the expandable strap that acts as a spring, and retains the mask on the patient both in the sniff position, and in the natural or "vertical" position.

Figure 28:
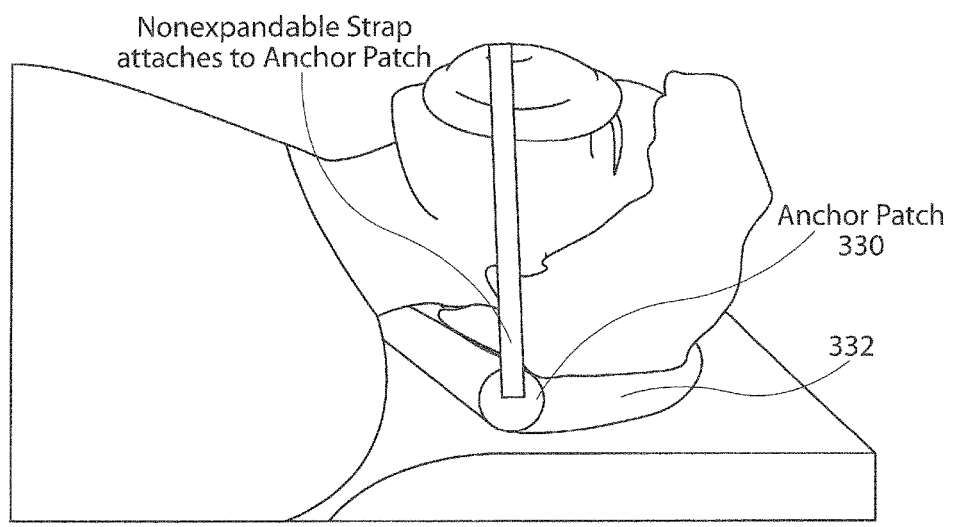
FIG. 28 is a side view showing an alternative embodiment in which the mask strap is attached to a patient head support in accordance with the present invention'

Referring to FIG. 28, in an alternate application, the left and right non-expandable straps could attach to the loop surface of anchor patches which are part of a patient head support 332, or any other structure mounted to the operating room table. This embodiment restrains the patient's head to the operating room table.

Figure 29:
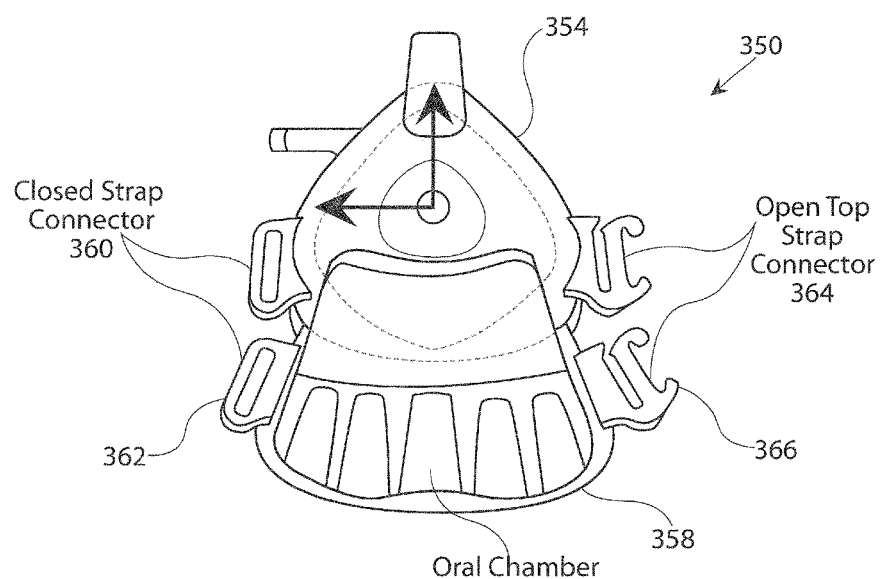
FIG. 29 is a top plan view of a combined nasal and mouth ventilation mask in accordance with the present invention.
Figure 30A:
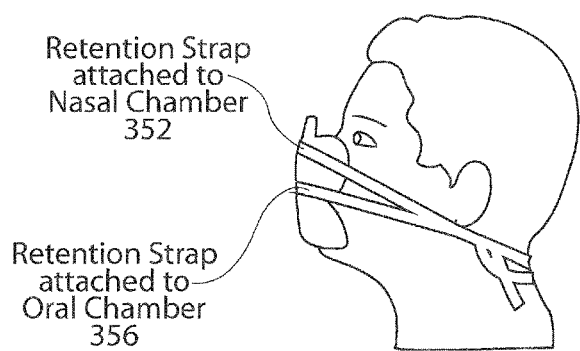
FIG. 30A and FIG. 30B are side and front views showing the mask of FIG. 29 attached to a patient.
Figure 30B:
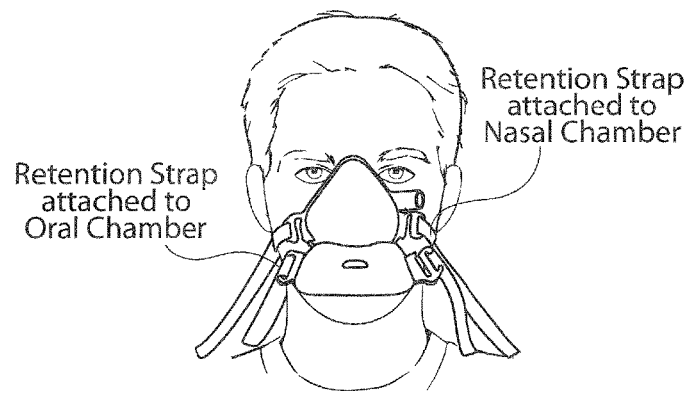

Referring to FIGS. 29 and 30, in yet another embodiment, the mask comprises a combined nasal and mouth ventilation mask detachably connected to one another so that the nasal mask and the mouth mask may be used either separately as a nasal mask, or as a combination nasal-mouth mask as above described. In such embodiment the seals or membranes on both the nasal mask and the mouth mask preferably comprise multi-lobe "Y"-shaped seals as above described. With this embodiment, the mask 350 is held on the patient with two (2) straps, one strap pair 352 attached to the nasal chamber 354, and a second strap pair 356 attached to the oral chamber 358. Strap pairs 352 and 356 are threaded through closed strap connectors 360, 362 and open strap connectors 364 and 366 provided on the sides of the nasal and oral chambers 354 and 358, respectively. As described in connection with FIGS. 26A and 26B, the retention straps preferably include first expandable strap portions, and second and third non-expandable strap portions. In another embodiment (not shown) both strap connectors could be closed or both could be open. Adding strap connectors and retention straps to the oral chamber 358 as shown in FIG. 29 permits one to achieve a better mask-to-face seal. Also, by providing separate and independently adjustable straps for the nasal chamber and the oral chamber, a better seal may be achieved. The resulting combination of a full face mask as above described with straps as above described, can provide a seal that supports a positive pressure greater than 20 cm $H_2O$ with attachment of the strap only, or with a nasal chamber held only by a strap can provide a seal that supports a positive pressure of greater than 30 cm $H_2O$. And, a full face mask as above described can provide a seal that supports a positive pressure greater than 40 cm $H_2O$ with that clinician placing it over the patient's face with the single hand, or with a nasal chamber only can provide a seal that supports a positive pressure greater than 40 cm H₂O with that clinician placing it over the patient's face with a single hand.

Figures 31A, 31B:
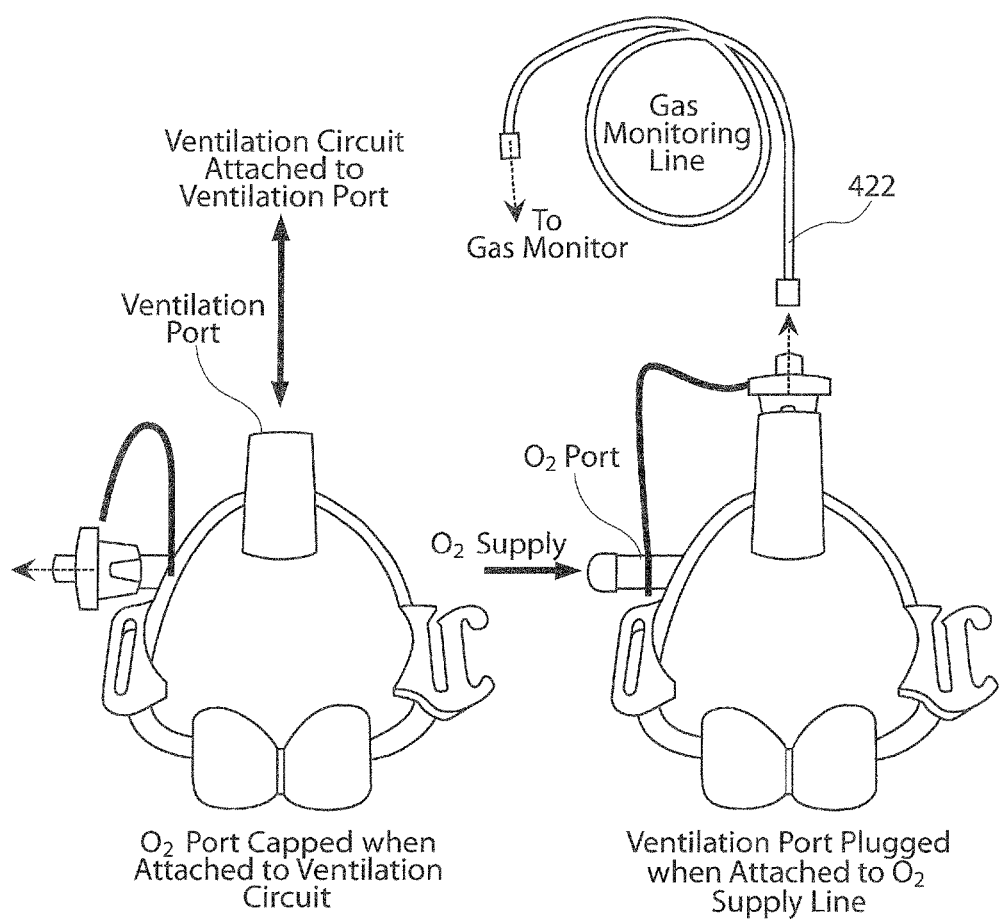
FIGS. 31A-31E are similar to FIGS. 20A-20E, and illustrate how a luer connector may be integrated into a cap valve for accommodating a gas monitoring line.
Figures 31C, 31D, 31E:
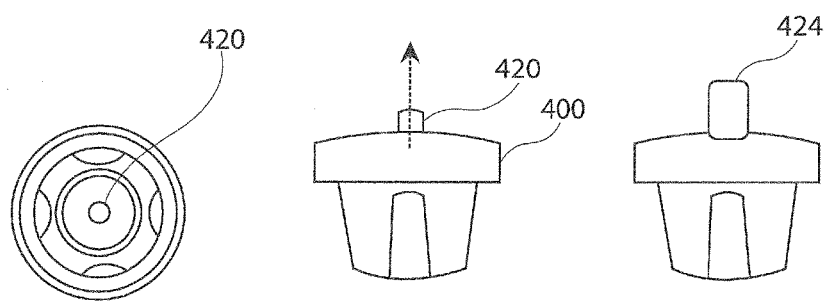

Various changes may be made in the above invention without departing from the spirit and scope thereof. Referring to FIGS. 31A-31E, a luer connector 420 may be integrated into the cap valve 400. With the luer connector 420 integrated into the cap valve 400, gases such as $CO_2$ being exhaled by a patient can occur when the ventilation mask is attached to a ventilation circuit via the ventilation port as shown in FIG. 31A where the $O_2$ port is capped but a gas monitoring line is attached to the luer connector 420. The $CO_2$ levels can also be monitored when an $O_2$ line is connected to the mask via the $O_2$ port in a CPAP or PEEP configuration as shown in FIG. 31B. In this configuration the gas monitoring line is attached to the luer connector integrated into the cap valve 400 which, in turn, is connected to a gas monitor. If the gas monitoring line is not connected to the luer connector, the luer connector can be capped by a cap 422, preventing gas from leaking through the associated port. Also, in place of hook and loop fasteners, the non-expandable straps may be threaded through a mechanical clasp such as a gripper of suspender-type no-slip clasp or grip; a button and buttonhole, snaps, a tab and belt hole clasp or the like. Still other changes are possible. For example, while the present invention has been described in connection with gas ventilation masks for use in delivering anesthesia, oxygen, etc. in medical settings, the combination nasal and mouth mask advantageously may be used, for example, for safety or gas masks or the like.

What is claimed:

1. A method of ventilating a patient, comprising:
    applying a nasal mask over the patient's nose while leaving the patient's mouth uncovered, wherein the nasal mask having at least one opening, the at least one opening comprising a septum or valve therein, a closing of the septum or valve is actuated by pressure within the mask, and wherein the nasal mask further comprises a ventilation and/or oxygen port, wherein the at least one opening is adapted to receive a fluid passage of an oral chamber,
    inserting the fluid passage of the oral chamber into the at least one opening, thereby causing the septum or valve to open and to allow fluid communication through the fluid passage between the oral chamber and the nasal mask, and
    flowing a gas into the nasal mask through the ventilation and/or oxygen port to pressurize the nasal mask, and receiving the gas and exhalation of the patient from the nasal mask through the ventilation and/or oxygen port.

2. The method of claim 1, wherein the septum or valve is a flexible duckbill valve.

3. The method of claim 1, wherein the at least one opening is adapted to receive a fluid passage of any of a gas scavenger, a gas collector, a nebulizer port, a PEEP valve port, and an expiratory port and/or valve.

4. The method of claim 1, wherein inserting the fluid passage of the oral chamber into the at least one opening comprises inserting a proboscis tube of the oral chamber into the at least one opening.

5. The method of claim 1, comprising separating the oral chamber from the nasal mask to seal the septum or valve.

6. The method of claim 1, wherein the nasal mask comprises a ventilation port and an oxygen port, and wherein the oxygen port is separate from the ventilation port.

7. The method of claim 1, wherein flowing a gas into the nasal mask comprises providing the same pressure level at the nasal mask and the oral chamber.

8. The method of claim 1, wherein the fluid passage is formed of a flexible material.

9. The method of claim 8, further comprising moving the oral chamber relative to the nasal mask.

10. A method of ventilating a patient, comprising:
    applying a nasal mask over the patient's nose while leaving the patient's mouth uncovered, wherein the nasal mask having at least one opening, the at least one opening comprising a septum or valve therein, a closing of the septum or valve is actuated by pressure within the mask, and wherein the nasal mask further comprises a ventilation and/or oxygen port, wherein the at least one opening is adapted to receive a fluid passage of an oral chamber;
    flowing a gas into the nasal mask through the ventilation and/or oxygen port to pressurize the nasal mask; and
    when the nasal mask is applied over the patient's nose, inserting the fluid passage of the oral chamber into the at least one opening, thereby causing the septum or valve to open and to allow fluid communication through the fluid passage between the oral chamber and the nasal mask.

11. The method of claim 10, wherein inserting the fluid passage of the oral chamber into the at least one opening comprises inserting a proboscis tube of the oral chamber into the at least one opening.

12. The method of claim 10, wherein the nasal mask comprises a ventilation port and an oxygen port, and wherein the oxygen port is separate from the ventilation port.

13. The method of claim 10 wherein flowing a gas into the nasal mask comprises providing the same pressure level at the nasal mask and the oral chamber.

* * * * *